(12) United States Patent
Choi et al.

(10) Patent No.: US 11,557,732 B2
(45) Date of Patent: Jan. 17, 2023

(54) ORGANIC ELECTROLUMINESCENT COMPOUND, AND ORGANIC ELECTROLUMINESCENT ELEMENT AND DEVICE EMPLOYING THE SAME

(71) Applicant: DUK SAN NEOLUX CO., LTD., Cheonan-si (KR)

(72) Inventors: Seung Won Choi, Cheonan-si (KR); Won Sam Kim, Cheonan-si (KR); Jung Hwan Park, Cheonan-si (KR); Chi Hyun Park, Cheonan-si (KR); Sun Hee Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 329 days.

(21) Appl. No.: 15/733,050

(22) PCT Filed: Sep. 19, 2018

(86) PCT No.: PCT/KR2018/011039
§ 371 (c)(1),
(2) Date: Apr. 30, 2020

(87) PCT Pub. No.: WO2019/088447
PCT Pub. Date: May 9, 2019

(65) Prior Publication Data
US 2020/0358004 A1    Nov. 12, 2020

(30) Foreign Application Priority Data
Oct. 30, 2017    (KR) .................. 10-2017-0142050

(51) Int. Cl.
*H01L 51/00*    (2006.01)
*C07D 491/048*    (2006.01)
(Continued)

(52) U.S. Cl.
CPC ...... *H01L 51/0072* (2013.01); *C07D 491/048* (2013.01); *C07D 495/04* (2013.01);
(Continued)

(58) Field of Classification Search
CPC ...... H01L 51/0071–0074; C07D 49/04; C07D 49/048; C09K 11/06
(Continued)

(56) References Cited

U.S. PATENT DOCUMENTS

2016/0028020 A1* 1/2016 Lee ................. H01L 51/0071
257/40

FOREIGN PATENT DOCUMENTS

CN    108884102    * 11/2018    ........... C07D 487/04
KR    10-2012-0132815 A    12/2012
(Continued)

Primary Examiner — Sheng-Bai Zhu
(74) Attorney, Agent, or Firm — Vorys, Sater, Seymour and Pease LLP; Mih Suhn Koh

(57) ABSTRACT

Provided are a compound represented by Formula 1, an organic electroluminescent element comprising a first electrode, a second electrode, and an organic material layer formed between the first electrode and the second electrode, and electroluminescent device thereof, and by comprising the compound represented by Formula 1 in the organic material layer, the driving voltage of the organic electroluminescent element can be lowered, and the luminous efficiency and life time of the organic electroluminescent element can be improved.

10 Claims, 1 Drawing Sheet

(51) Int. Cl.
   *C07D 495/04*     (2006.01)
   *C09K 11/06*      (2006.01)
   *H01L 51/50*      (2006.01)
(52) U.S. Cl.
   CPC .......... *C09K 11/06* (2013.01); *H01L 51/0071* (2013.01); *H01L 51/0073* (2013.01); *H01L 51/0074* (2013.01); *C09K 2211/1018* (2013.01); *H01L 51/5016* (2013.01)
(58) Field of Classification Search
   USPC ....................................................... 428/690
   See application file for complete search history.

(56)      References Cited

FOREIGN PATENT DOCUMENTS

| | | | |
|---|---|---|---|
| KR | 10-2016-0012895 A | 2/2016 | |
| KR | 10-2017-0112865 A | 10/2017 | |
| KR | 10-2017-0113334 A | 10/2017 | |
| KR | 10-2017-0119291 A | 10/2017 | |
| WO | WO-2012165844 A1 * | 12/2012 | ........... C07D 401/14 |

\* cited by examiner

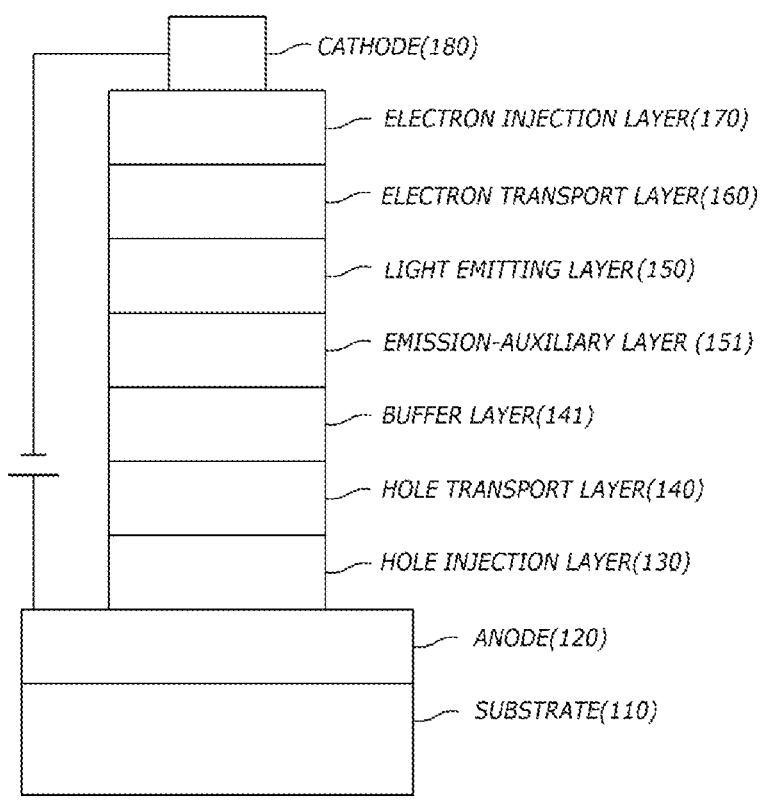

ORGANIC ELECTROLUMINESCENT COMPOUND, AND ORGANIC ELECTROLUMINESCENT ELEMENT AND DEVICE EMPLOYING THE SAME

CROSS-REFERENCE TO RELATED APPLICATION

This patent application claims priority from and the benefit under 35 U.S.C. § 119 to § 121, and § 365 of Korean Patent Application No. 10-2017-0142050, filed on Oct. 30, 2017, which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for organic electroluminescent element, organic electroluminescent elements using the same, and electronic devices thereof.

Background Art

In general, an organic light emitting phenomenon refers to a phenomenon in which electric energy is converted into light energy of an organic material. An organic electroluminescent element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electroluminescent element, and for example, may include a hole injection layer, a hole transport layer, a light emitting layer, an electron transport layer, an electron injection layer, or the like.

Materials used as an organic material layer in an organic electroluminescent element may be classified into a light emitting material and a charge transport material, for example, a hole injection material, a hole transport material, an electron transport material, an electron injection material, and the like according to its function. In addition, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Also, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according to the type of the dopant.

Currently, the power consumption greater than that required in the existing portable display is required as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light-emitting material that has high thermal stability and can efficiently achieve charge balance in the light-emitting layer. That is, in order to allow an organic electroluminescent element to fully exhibit its excellent features, it should be prerequisite to support a material constituting an organic material layer in the element, for example, a hole injection material, a hole transport material, a light emitting material, an electron transport material, an electron injection material, or the like, by a stable and efficient material. However, the development of stable and efficient organic material layer materials for organic electroluminescent element has not been sufficiently achieved, and accordingly, in particular, it is strongly required to develop host material of a light emitting layer.

Object, Technical Solution and Effects of the Invention

The object of the present invention is to provide a compound capable of lowering driving voltage of the element, and improving luminous efficiency and lifetime, an organic electroluminescent element employing the same, and an electronic device thereof.

In accordance with an aspect of the present invention, the compound represented by the following formula is provided.

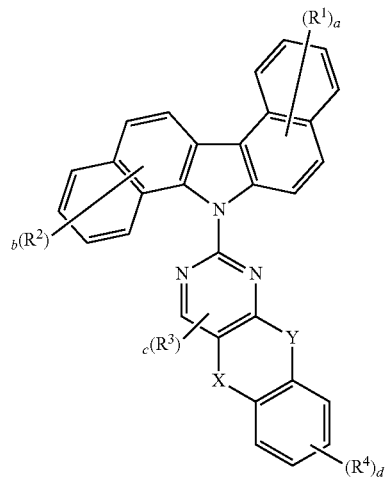

In another aspect of the present invention, an organic electroluminescent element employing the compound represented by the above formula and an electronic device comprising the organic electroluminescent element are provided.

According to the present invention, by employing a compound according to one embodiment of the present invention, the driving voltage of a device can be lowered, and the luminous efficiency and lifetime of a device can be significantly improved.

BRIEF DESCRIPTION OF THE DRAWINGS

The FIGURE illustrates an example of an organic electroluminescent element according to an embodiment of the present invention: 100 is organic electroluminescent element, 110 is a substrate, 120 is first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

DETAILED DESCRIPTION

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the Spiro compound together with the carbon to which they are bonded.

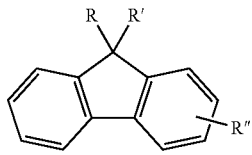

Unless otherwise stated, the term "heterocyclic group" as used herein means a ring comprising a heteroatom such as N, O, S, P, Si and the like, it comprises a non-aromatic ring as well as an aromatic ring such as "a heteroaryl group" or "a heteroarylene group". Also, the term "heterocyclic group" may comprise a ring including a heteroatom group such as $SO_2$, $P=O$ and the like instead of a carbon consisting of a ring. For example, "heterocyclic group" includes the following compound.

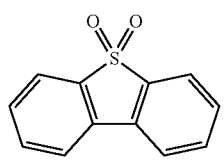 [SMILES: O=S1(=O)c2ccccc2-c2ccccc21]

The term "spiro compound" as used herein has, a spiro union which means union having one atom as the only common member of two rings. The common atom is designated as 'spiro atom'. The compounds are defined as 'monospiro-', 'dispiro-' or 'trispiro' depending on the number of spiro atoms in one compound.

In addition, otherwise specified, the formulas used in the present invention are as defined in the index definition of the substituent of the following formula.

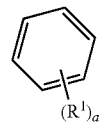

Here, when a is an integer of zero, the substituent $R^1$ is absent, when a is an integer of 1, $R^1$ is linked to any one of the carbon atoms constituting the benzene ring, when a is an integer of 2 or 3, the substituent $R^1$s are linked to the benzene ring as follows and the substituent $R^1$s may be the same and different. When a is an integer of 4 to 6, the substituents $R^1$s are linked to the benzene ring in a similar manner to that when a is an integer of 2 or 3, hydrogen linked to carbon constituents of the benzene ring may be omitted.

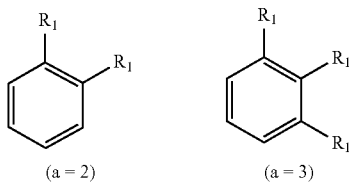

Hereinafter, a laminated structure of the electroluminescent element comprising the compound of the present invention will be described with reference to FIGURE.

The FIGURE illustrates a laminated structure of the electroluminescent element according to an embodiment of the present invention.

Referring to the FIGURE, an organic electroluminescent element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

In addition, although not shown, the organic electroluminescent element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, electron transport layer 160, an electron injection layer 170, a light emitting layer 150, a layer for improving luminous efficiency, an emission-auxiliary layer and so on. For example, the inventive compound may be used as material of the light emitting layer 150, preferably, as host material of the light emitting layer.

The organic electroluminescent element according to an embodiment of the present invention may be manufactured using various deposition methods. The organic electroluminescent element according to an embodiment of the present invention may be manufactured using a PVD (physical vapor deposition) method or CVD (chemical vapor deposition) method. For example, the organic electroluminescent element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

Also, the organic electroluminescent element according to an embodiment of the present invention may be any one of an organic light emitting diode, an organic solar cell, an organic photo conductor, an organic transistor, an element for monochromatic or white illumination and an element for quantum dot display.

Another embodiment of the present invention provides an electronic device including a display device which includes the above described organic electroluminescent element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers, and the above a display device may comprise an organic electroluminescent display, an quantum dot display and the like.

Hereinafter, the compound according to an aspect of the present invention will be described.

The compound according to an aspect of the present invention is represented by formula 1 below.

[Formula 1]

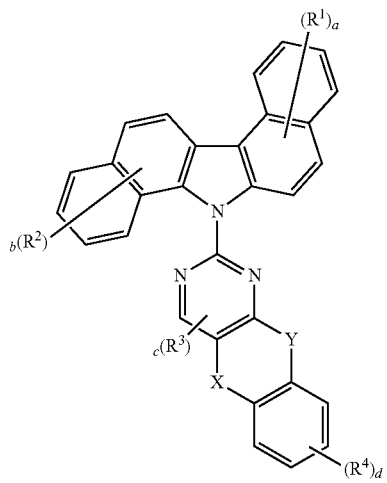

In the formula 1, each of symbols may be defined as follows.

$R^1$ to $R^4$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

In addition, adjacent $R^1$ groups, adjacent $R^2$ groups or adjacent $R^4$ groups together may be bonded to each other to form a $C_6$-$C_{60}$ aromatic ring or a $C_2$-$C_{60}$ heterocycle.

a and b represent an integer of 0-6, c represents an integer of 0 or 1, d represents an integer of 0-4, and when each of these is an integer of 2 or more, each $R^1$, each $R^2$, each $R^3$ or each $R^4$ may be the same or different from each other.

When $R^1$ to $R^4$ are an aryl group, $R^1$ to $R^4$ may be preferably a $C_6$-$C_{30}$ or $C_6$-$C_{20}$ aryl group, more preferably a $C_6$-$C_{14}$ aryl group, for example, phenyl, biphenyl, naphthyl, phenanthrene or the like; when $R^1$ to $R^4$ are a heterocyclic group, $R^1$ to $R^4$ may be preferably a $C_2$-$C_{30}$ or $C_2$-$C_{20}$ heterocyclic group, more preferably a $C_2$-$C_{12}$ heterocyclic group, for example, pyridine, pyrimidine, triazine, carbazole, dibenzofuran, dibenzothiophene or the like.

Preferably, $R^3$ may be a $C_6$-$C_{14}$ aryl group, a $C_2$-$C_{12}$ heterocyclic group, F, CN or the like.

Preferably, adjacent $R^4$ groups together may be bonded to each other to form a $C_6$-$C_{30}$ aromatic ring or $C_6$-$C_{20}$ aromatic ring, more preferably, $C_6$-$C_{14}$ aromatic ring, for example, benzene, naphthalene, phenanthrene and so on.

In addition, preferably, $R^3$ may be a $C_6$-$C_{14}$ aryl group, a $C_2$-$C_{12}$ heterocyclic group, F or CN and adjacent $R^4$ groups together may be bonded to each other to form a $C_6$-$C_{14}$ aromatic ring.

More preferably, R³ may be phenyl, biphenyl, naphthyl, phenanthrene, pyridine, pyrimidine, triazine, carbazole, dibenzofuran or dibenzothiophene, both R¹ and R² are hydrogen, and R⁴ may be hydrogen or adjacent R⁴ groups together may be bonded to each other to form a benzene ring.

X and Y are each independently a single bond, O or S, and at least one of X and Y is O or S. That is, the case where X and Y are both single bond is excluded. Preferably, one of X or Y is O and the other is S.

L' is selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring and a $C_2$-$C_{60}$ heterocyclic group.

$R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P.

The above R¹ to R⁴, L', $R_a$, $R_b$, and a ring formed by adjacent R¹ groups, adjacent R² groups or adjacent R⁴ groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group, and a $C_8$-$C_{20}$ arylalkenyl group.

For example, R¹ to R⁴ may be further substituted with deuterium or phenyl, and more preferably, R¹ to R³ may be substituted with deuterium.

Preferably, Formula 1 may be represented by Formula 2 or Formula 3 below.

<Formula 2>

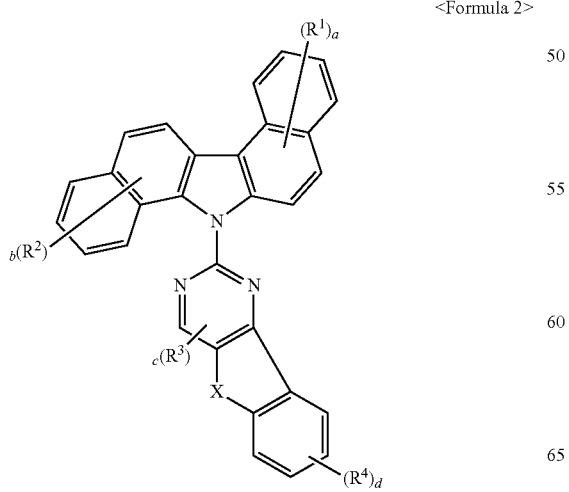

<Formula 3>

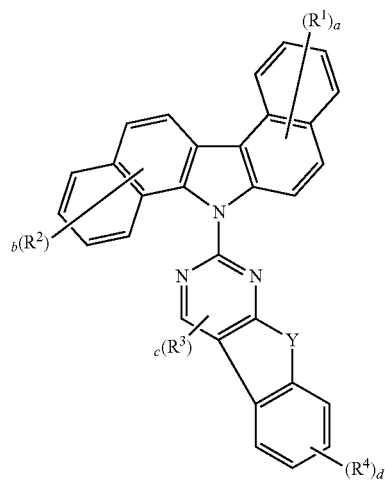

In Formulas 2 and 3, R¹ to R⁴, a, b, c, d, X and Y are the same as defined for Formula 1.

Specifically, the compound represented by formula 1 may be one of the following compounds.

1

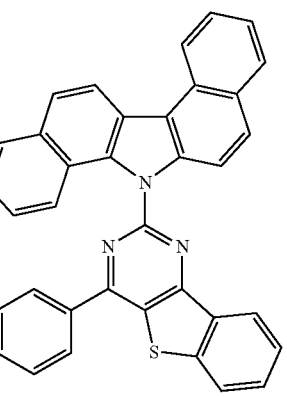

2

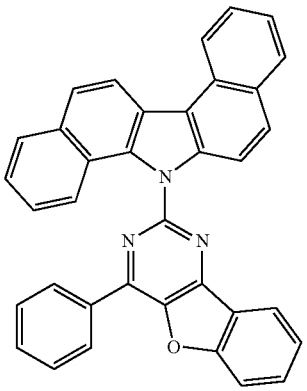

3
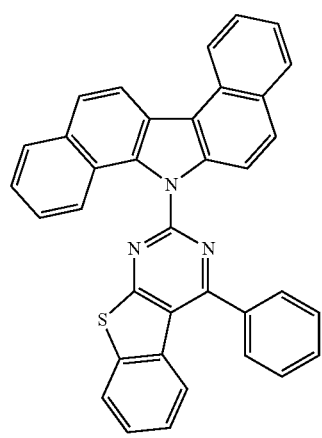
4
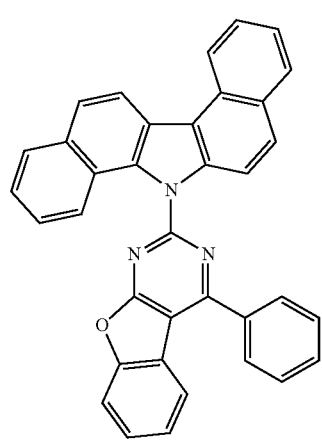
5
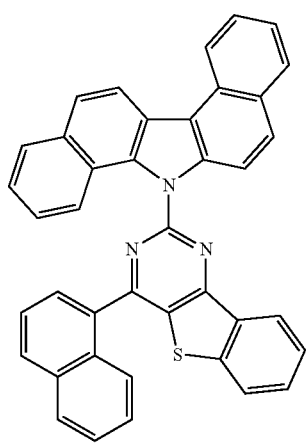
6
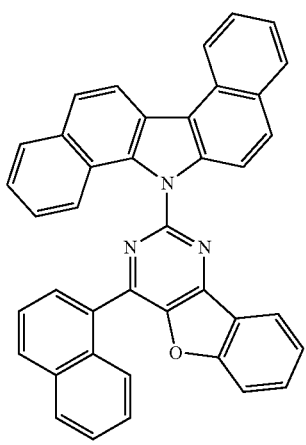
7
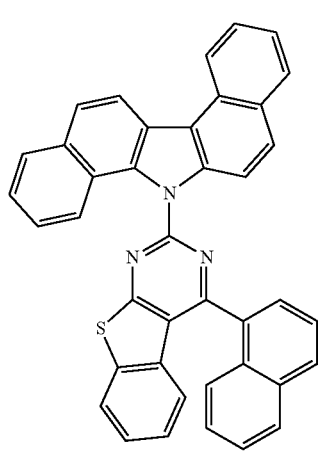
8
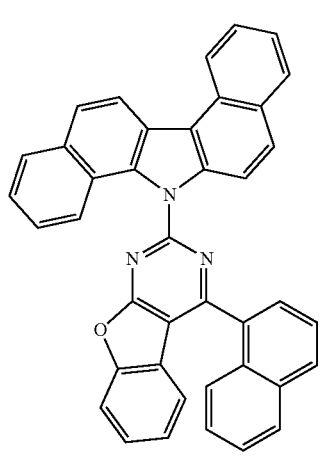

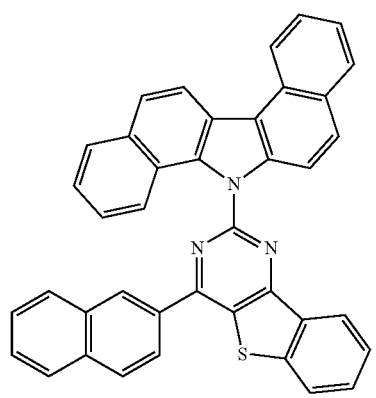
9
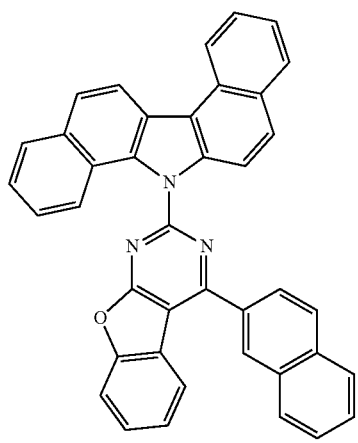
12
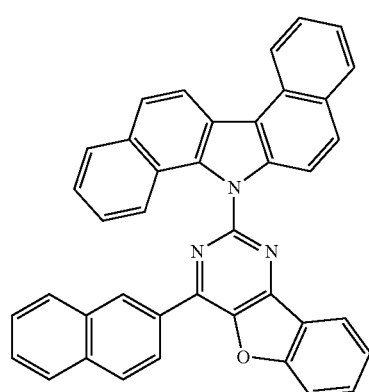
10
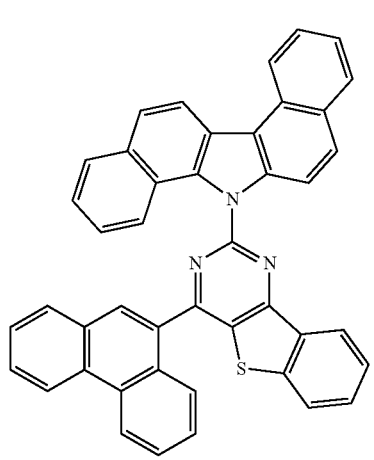
13
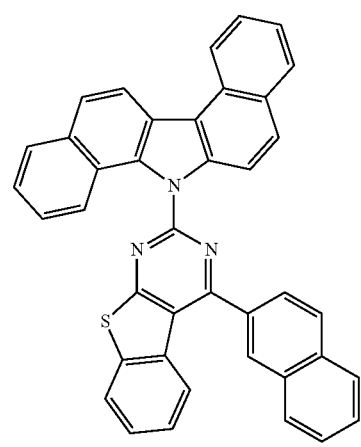
11
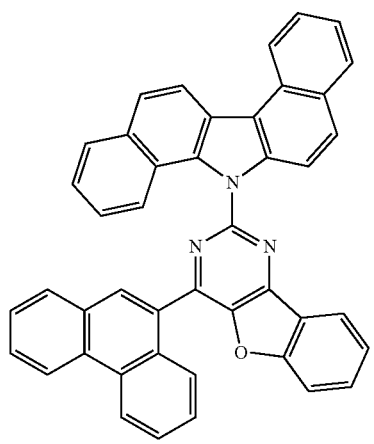
14

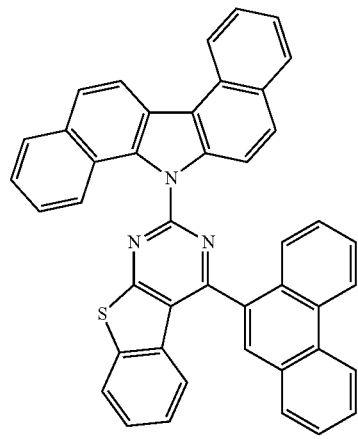
15
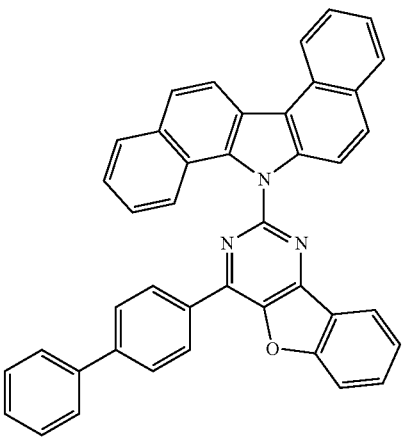
18
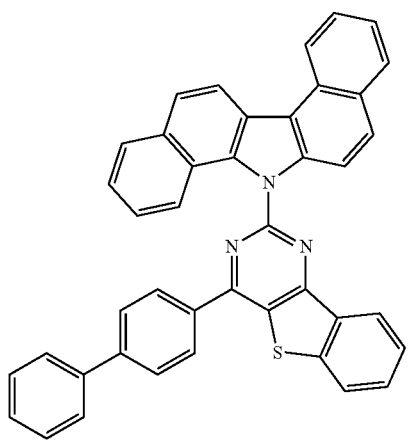
16
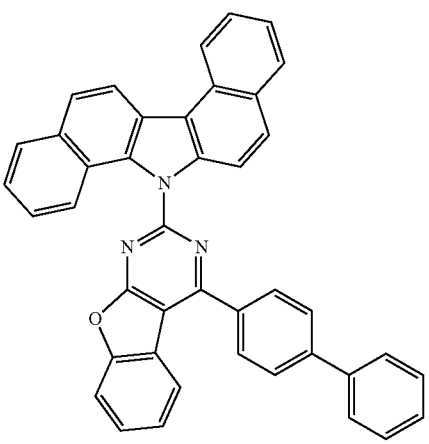
19
17
20

21
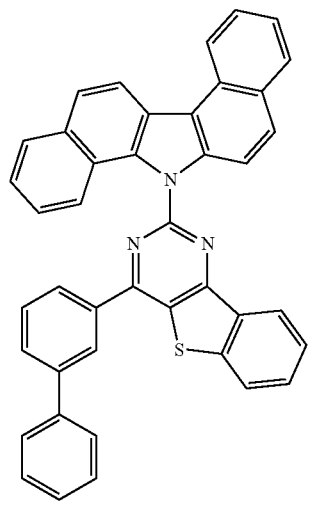
22
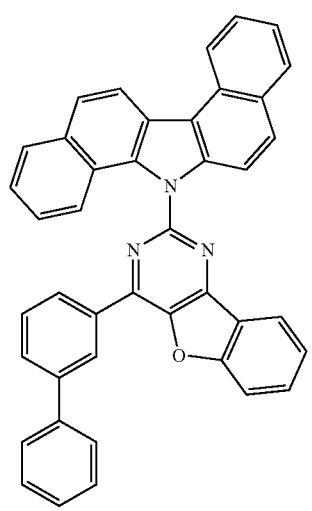
23
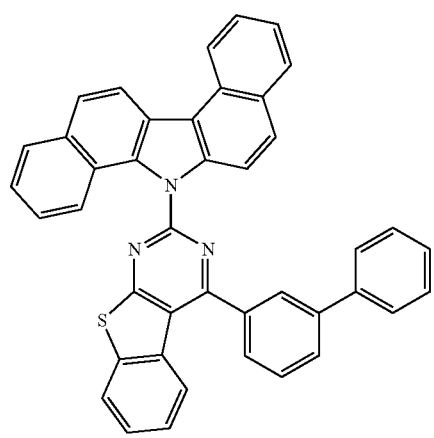
24
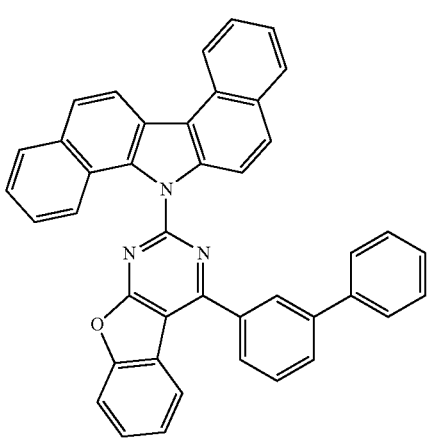
25
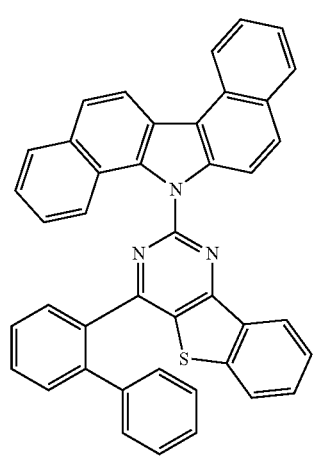
26
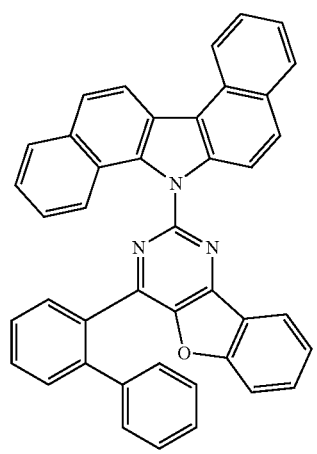

27
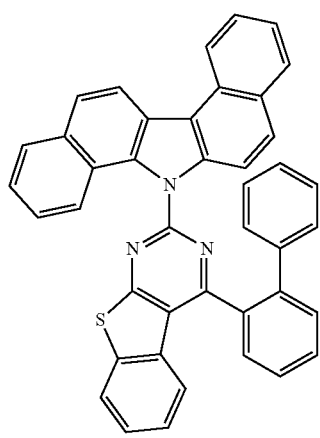
28
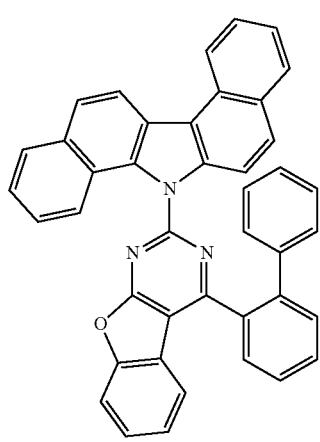
29
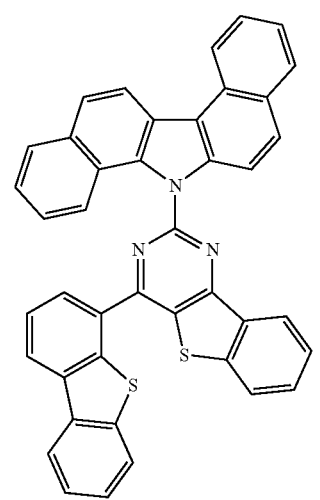
30
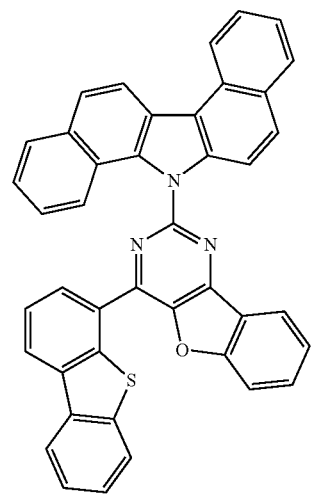
31
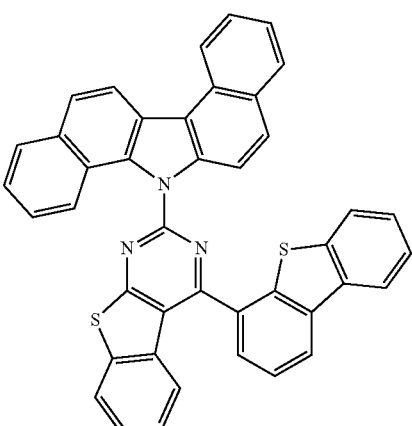
32
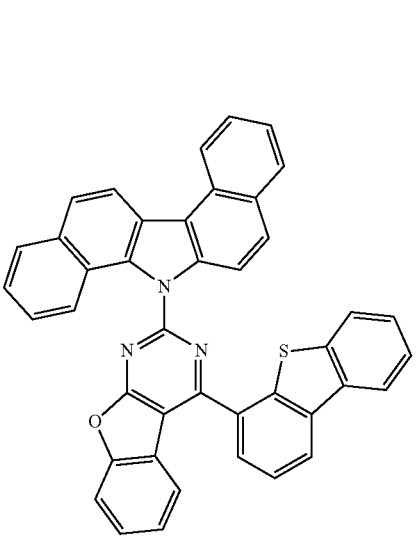

33
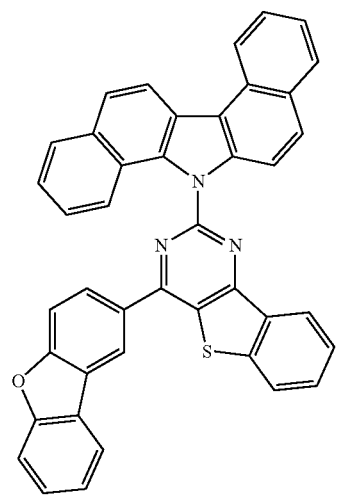
34
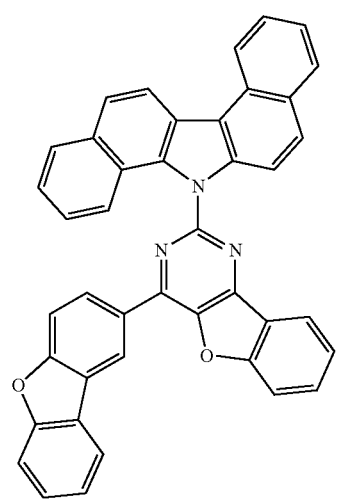
35
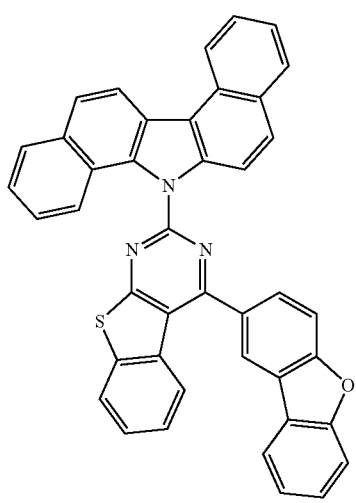
36
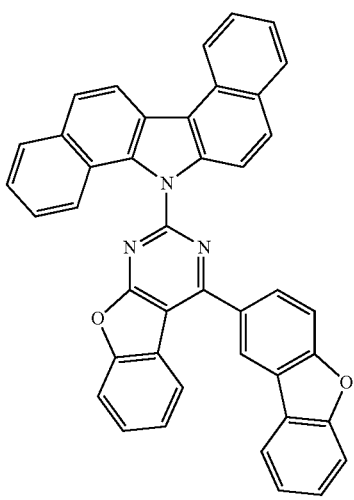
37
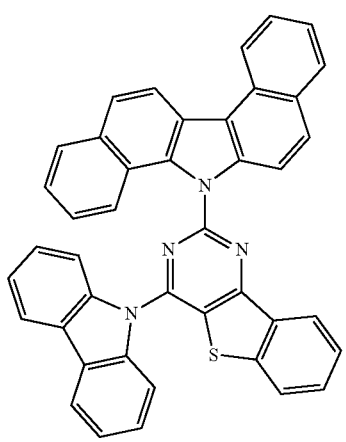
38
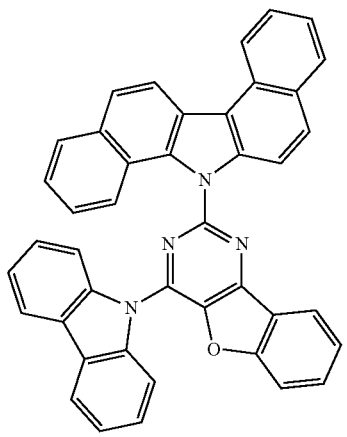

39
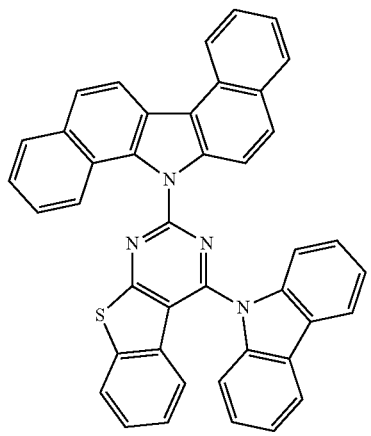
40
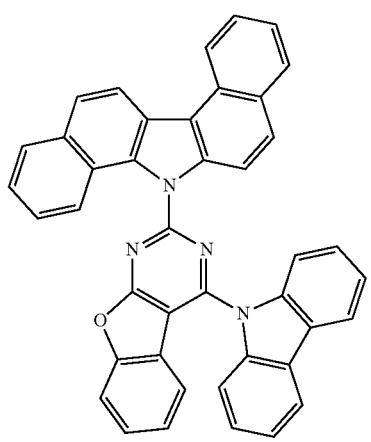
41
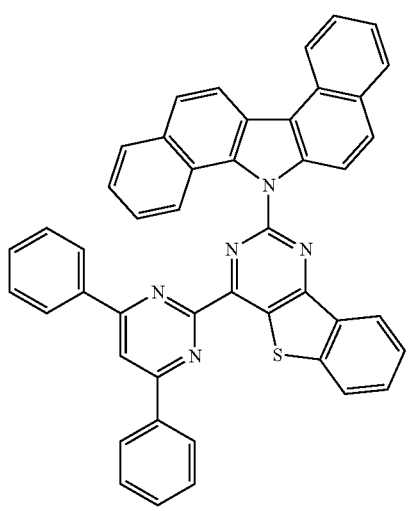
42
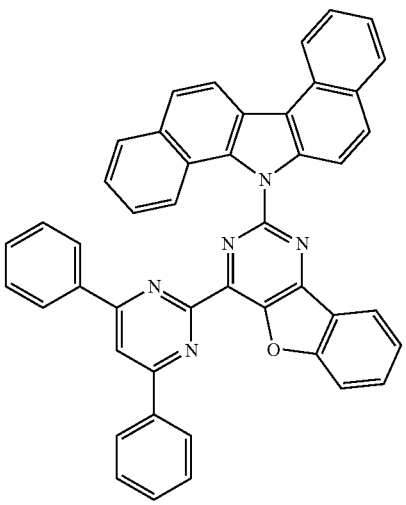
43
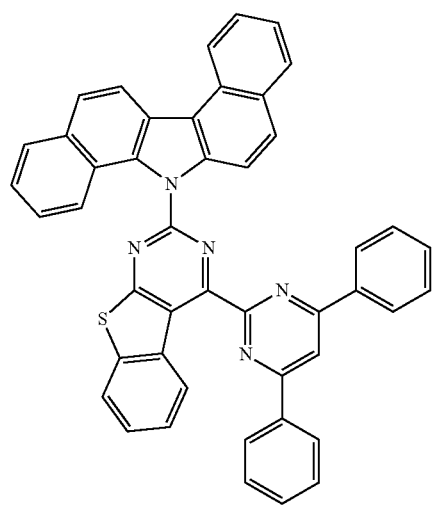
44
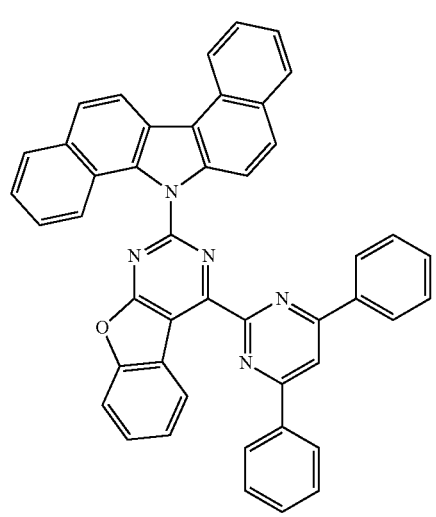

45
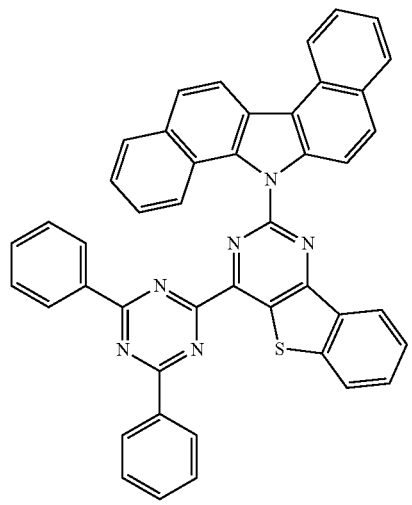
46
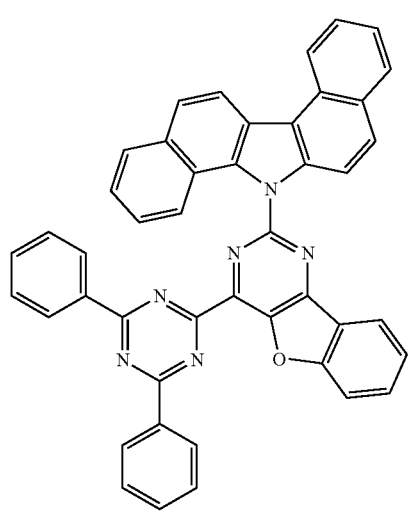
47
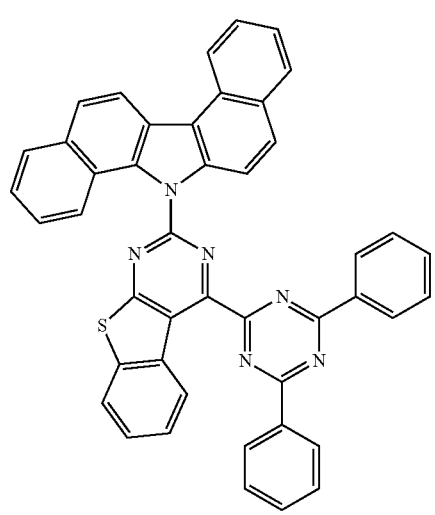
48
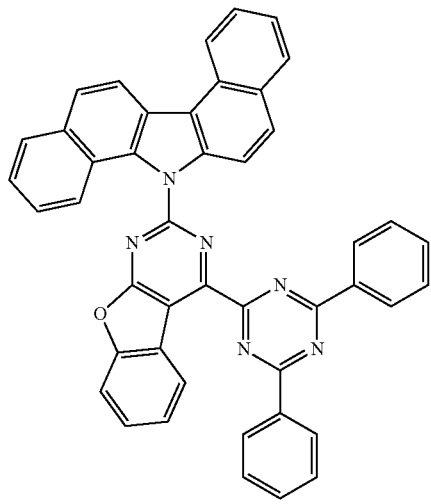
49
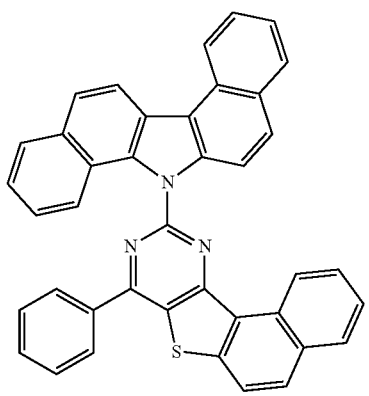
50
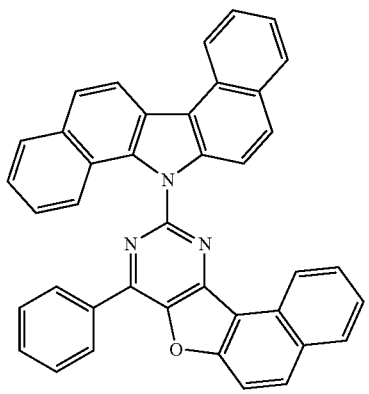

-continued
51
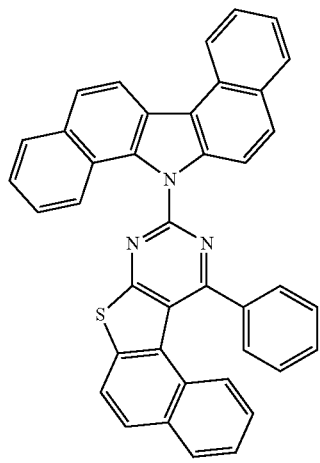
52
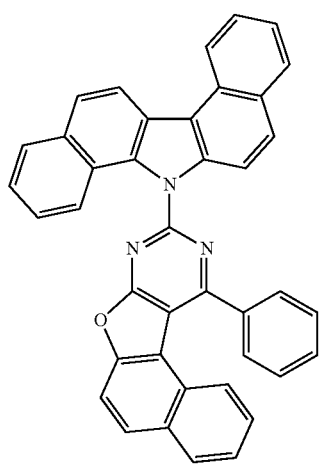
53
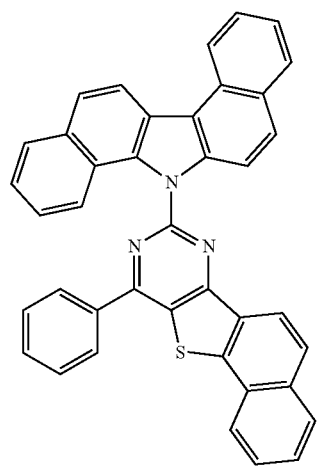
-continued
54
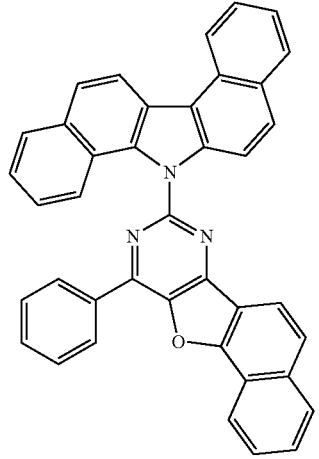
55
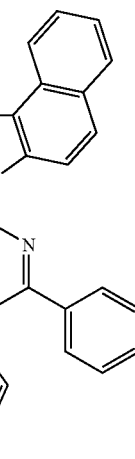
56
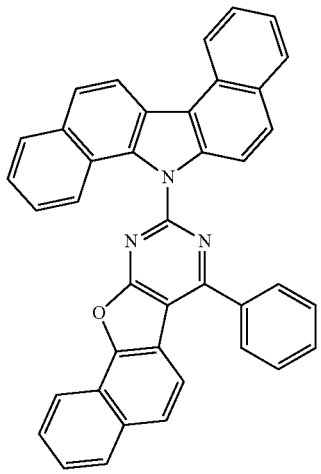

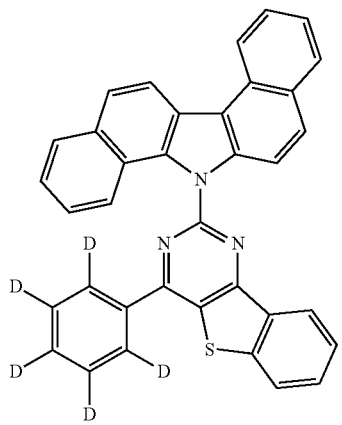

57

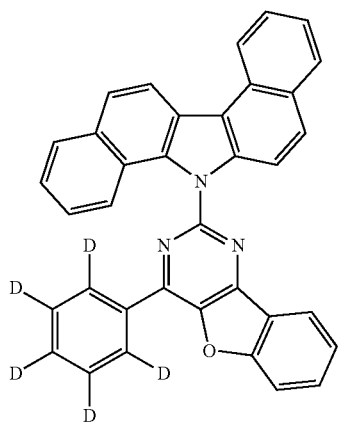

58

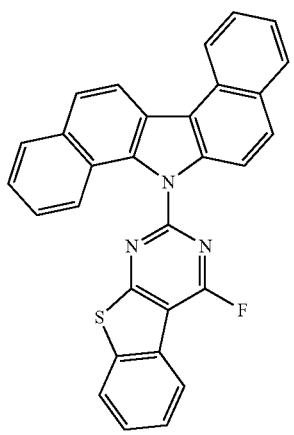

59

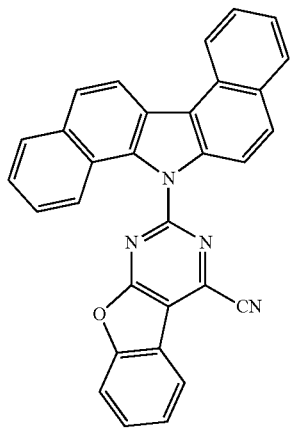

60

In another embodiment of the present invention, the present invention provides an organic electroluminescent element comprising a first electrode, a second electrode, and an organic material layer formed between the first electrode and the second electrode, wherein the organic material layer comprises a single compound or a mixture of the compound represented by Formula 1.

The organic material layer comprises at least one layer of a hole injection layer, a hole transport layer, an emission-auxiliary layer, a light emitting layer, an electron transport auxiliary layer, an electron transport layer and an electron injection layer, and preferably, the compound represented by the Formula 1 is comprised in the the light emitting layer.

In another embodiment of the present invention, the present invention provides an electronic device comprising a display device and a control unit for driving the display device, wherein the display device comprises the organic electroluminescent element.

Hereinafter, synthesis example of the compound represented by Formula 1 and preparation method of an organic electroluminescent element according to one embodiment of the present invention will be described in detail by way of examples. However, the present invention is not limited to the following examples.

SYNTHESIS EXAMPLE

The compound represented by Formula 1 according to the present invention can be synthesized by reacting Sub 1 and Sub 2 as shown in Reaction Scheme 1 below.

<Reaction Scheme 1>

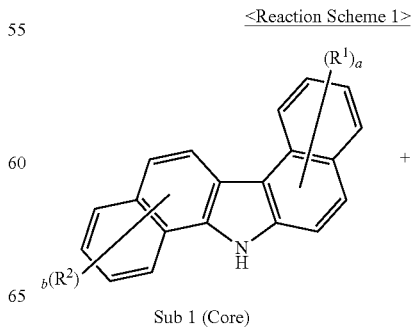

Sub 1 (Core)

-continued

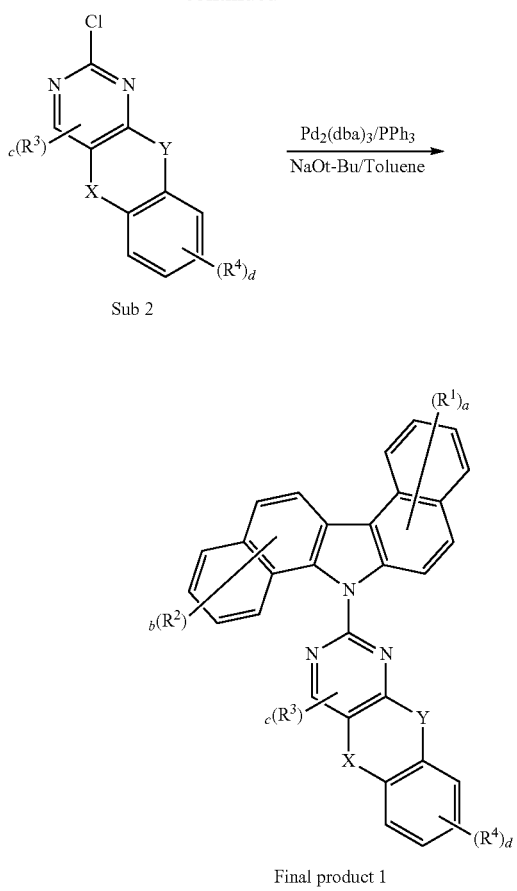

Sub 2

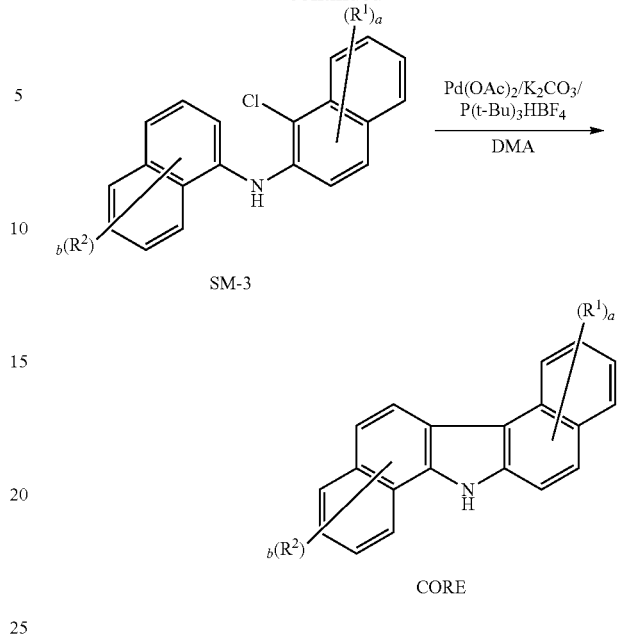

SM-3

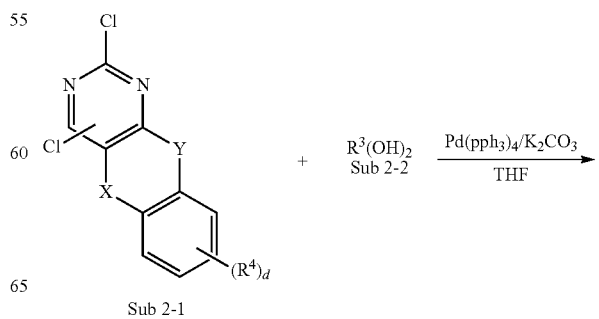

CORE

Final product 1

Synthesis Example of Sub 1

Sub 1 of the Reaction Scheme 1 may be synthesized by the reaction route of the following Reaction Scheme 2.

<Reaction Scheme 2>

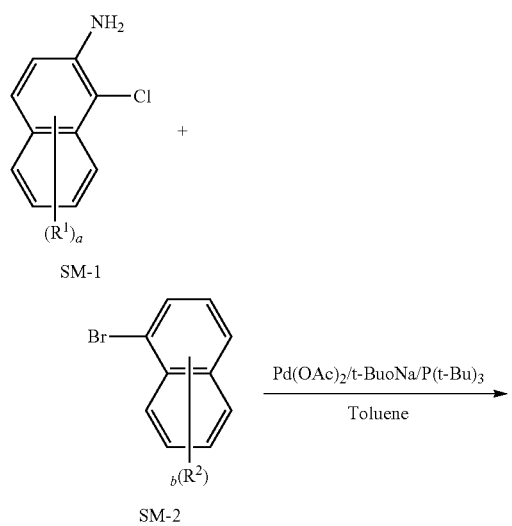

Synthesis Example of SM-3

After mixing SM-1 (1 eq.), SM-2 (1 eq.), Pd(OAc)$_2$ (0.03 eq.), P(t-Bu)$_3$ (0.1 eq.), t-BuONa (2 eq.) and toluene (4 mL/SM-1 1 mmol), the reaction proceeds at 60° C. When the reaction was completed, the reaction product was extracted with CH$_2$Cl$_2$ and water, and the organic layer was dried with MgSO$_4$ and concentrated. Thereafter, the concentrate was passed through a silica gel column and recrystallized to obtain SM-3 (yield: 84%).

Synthesis Example of Sub 1(Core)

After mixing SM-3 (1 eq.), Pd(OAc)$_2$ (0.03 eq.), P(t-Bu)$_3$ (0.1 eq.), K$_2$CO$_3$ (3 eq.) and DMA (8 mL/SM-3 1 mmol), the reaction proceeds at 180° C. When the reaction was completed, the reaction product was extracted with CH$_2$Cl$_2$ and water, and the organic layer was dried with MgSO$_4$ and concentrated. Thereafter, the concentrate was passed through a silica gel column and recrystallized to obtain CORE (yield: 82%).

Synthesis Example of Sub 2

Sub 2 of the Reaction Scheme 1 may be synthesized by the reaction route of the following Reaction Scheme 3.

<Reaction Scheme 3>

-continued

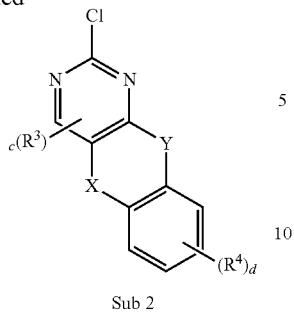

Sub 2

Synthesis of Sub 2(1a)

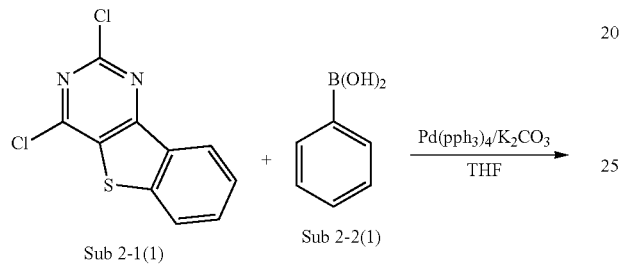

Sub 2(1a)

Sub 2-1 (1) (5.1 g, 20 mmol), Sub 2-2 (1) (2.9 g, 24 mmol), Pd(PPh$_3$)$_4$ (0.7 g, 0.6 mmol), NaOH (2.4 g, 60 mmol), THF (60 mL), and water (30 mL) were placed into a round bottom flask and the mixture was heated at 80-90° C. under reflux. When the reaction was completed, the reaction product was diluted by adding distilled water at room temperature and the resultant was extracted with CH$_2$Cl$_2$ and water. The organic layer was dried with MgSO$_4$ and concentrated. Thereafter, the concentrate was passed through a silica gel column and recrystallized to obtain 4.8 g of Sub 2(1a) (yield: 81%).

Synthesis of Sub 2(2a)

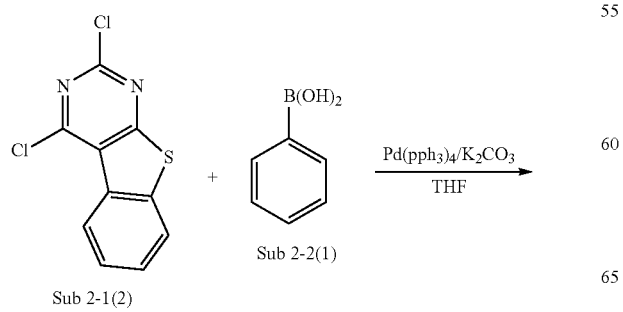

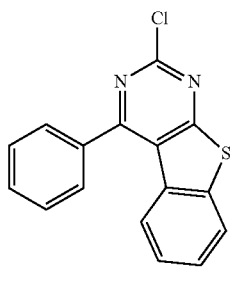

Sub 2(2a)

Sub 2-1(2) (5.1 g, 20 mmol), Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were placed into a round bottom flask and 5.0 g (yield: 85%) of Sub 2(2a) was obtained by using the same manner as in the synthesis method of Sub 1(1a).

Synthesis of Sub 2(3a)

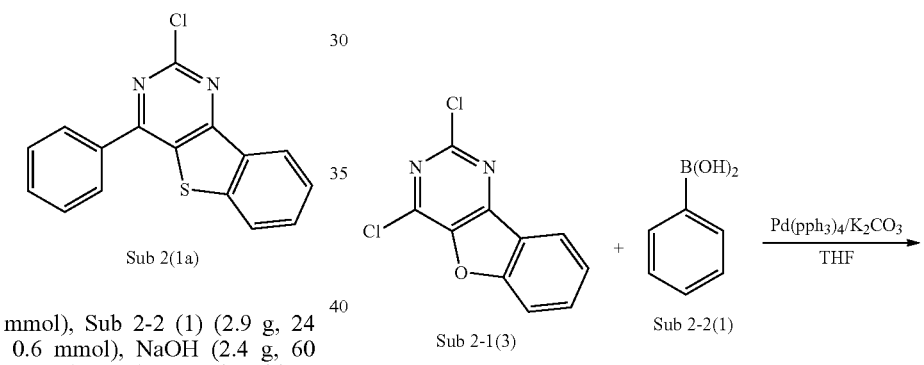

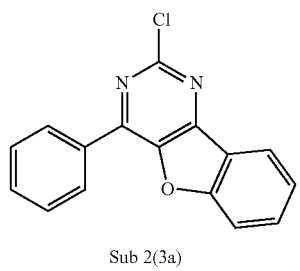

Sub 2(3a)

Sub 2-1(3) (4.8 g, 20 mmol), Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were placed into a round bottom flask and 4.9 g (yield: 87%) of Sub 2(3a) was obtained by using the same manner as in the synthesis method of Sub 1(1a).

Synthesis of Sub 2(4a)

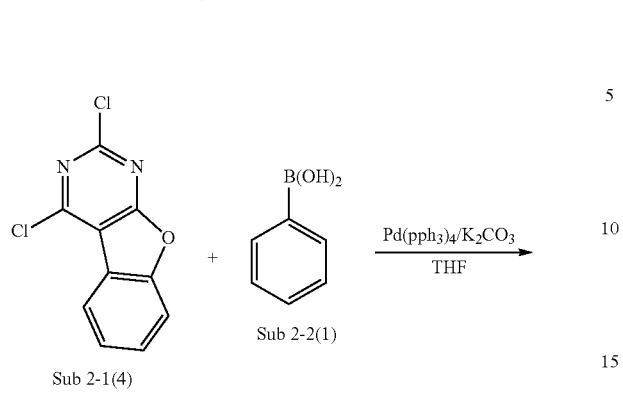

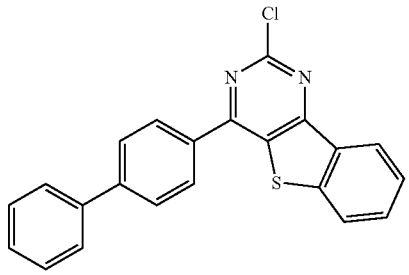

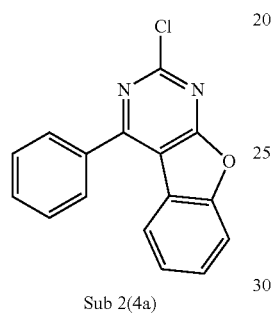

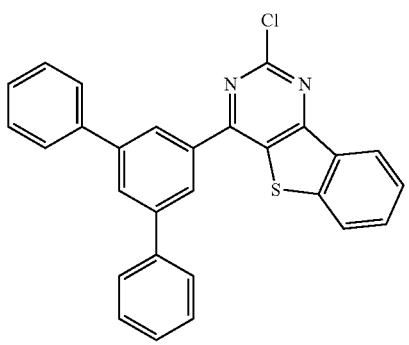

Sub 2-1(4) (4.8 g, 20 mmol), Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were placed into a round bottom flask and 5.0 g (yield: 89%) of Sub 2(4a) was obtained by using the same manner as in the synthesis method of Sub 1(1a).

The compounds belonging to Sub 2 synthesized by the synthesis above may be, but not limited to, the following compounds, and Table 1 shows the FD-MS values of the compounds belonging to Sub 2.

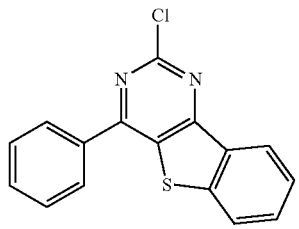

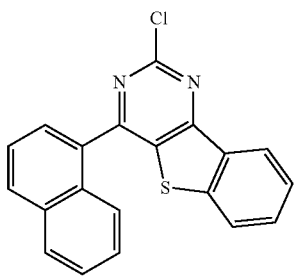

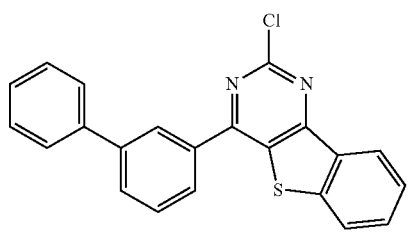

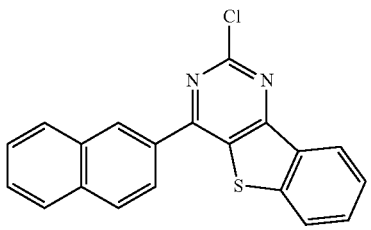

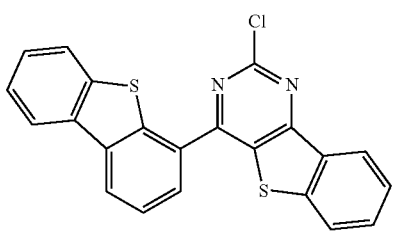

Sub 2(1h)
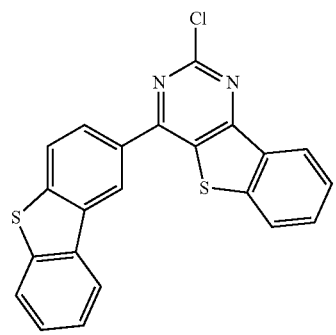
Sub 2(1i)
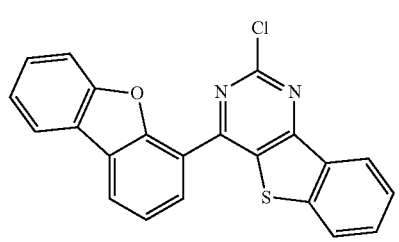
Sub 2(1j)
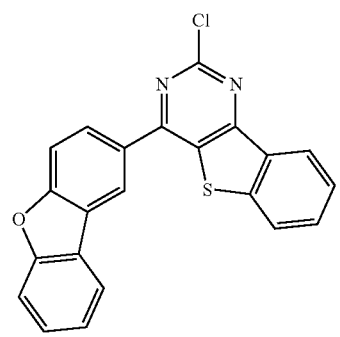
Sub 2(1k)
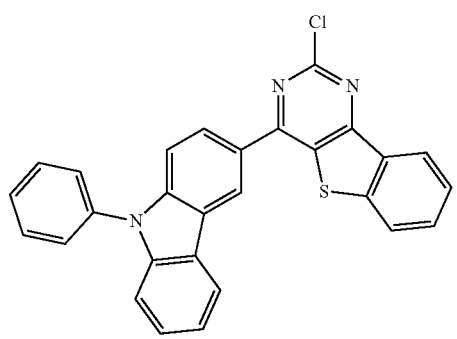
Sub 2(1l)
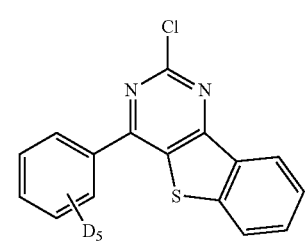
Sub 2(2a)
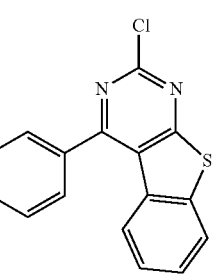
Sub 2(2b)
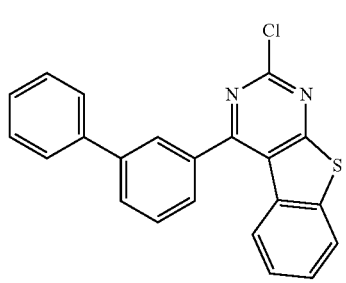
Sub 2(2c)
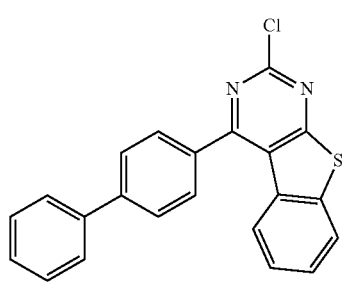
Sub 2(2d)
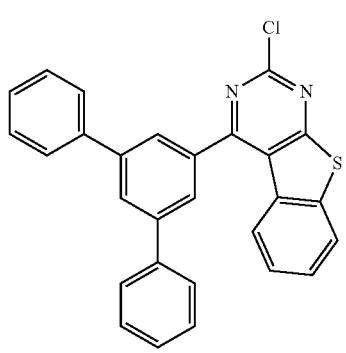
Sub 2(2e)
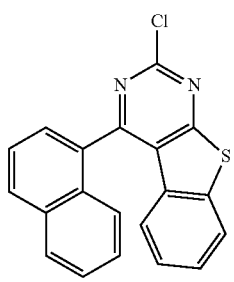

Sub 2(2f)
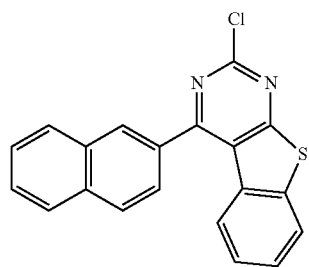
Sub 2(2g)
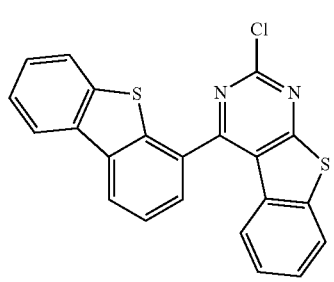
Sub 2(2h)
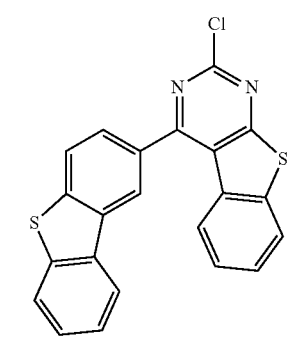
Sub 2(2i)
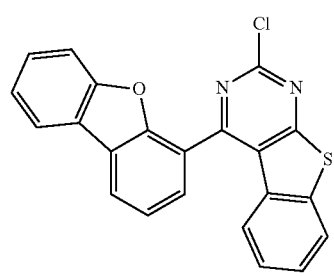
Sub 2(2j)
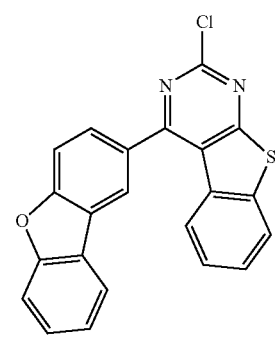
Sub 2(2k)
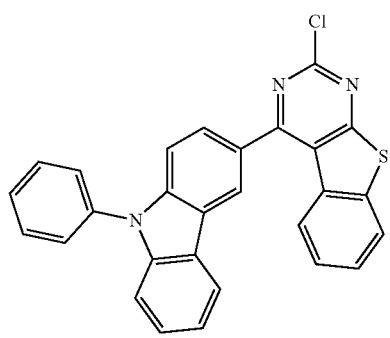
Sub 2(2l)
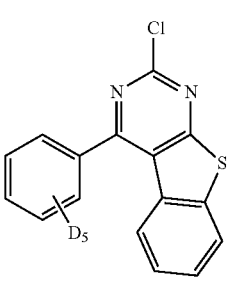
Sub 2(3a)
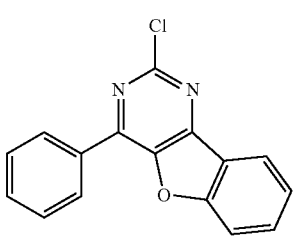
Sub 2(3b)
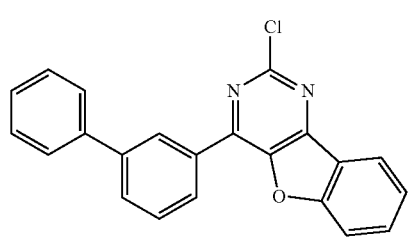
Sub 2(3c)
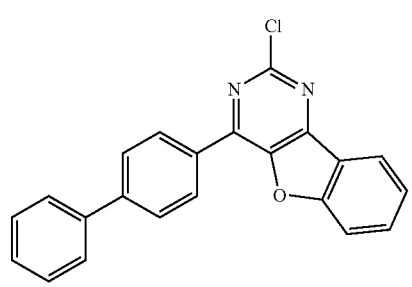

Sub 2(3d)
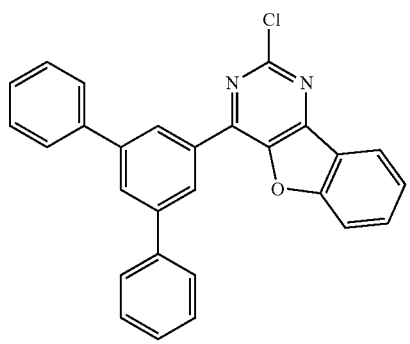
Sub 2(3e)
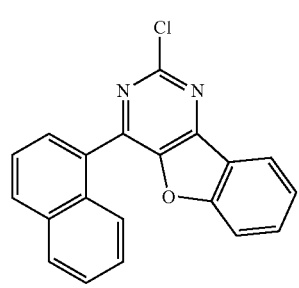
Sub 2(3f)
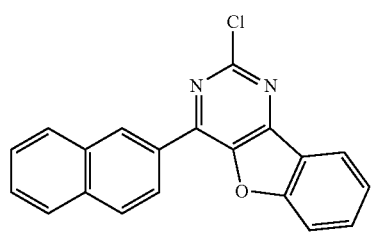
Sub 2(3g)
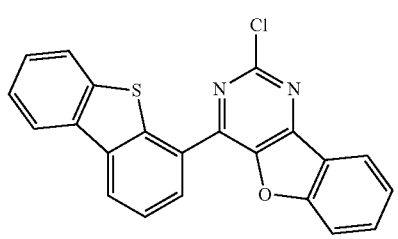
Sub 2(3h)
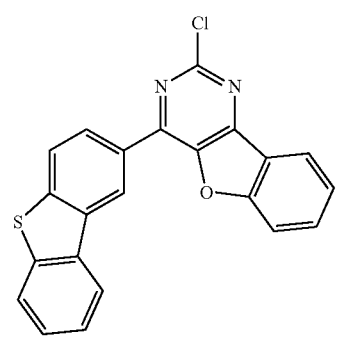
Sub 2(3i)
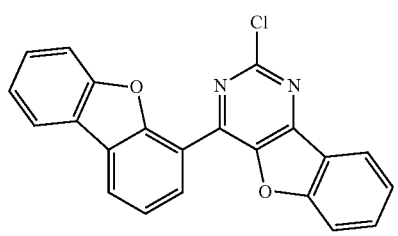
Sub 2(3j)
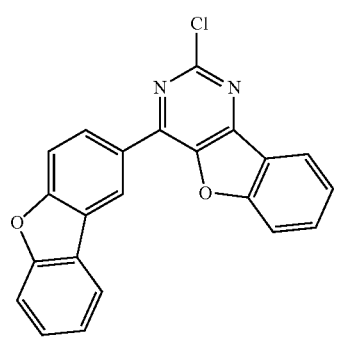
Sub 2(3k)
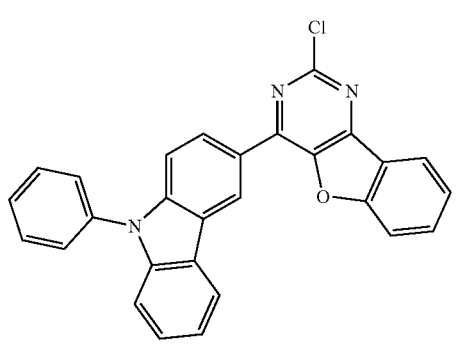
Sub 2(3l)
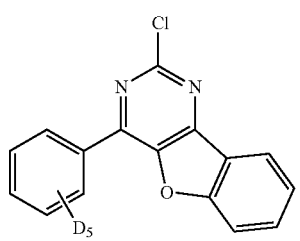
Sub 2(4a)
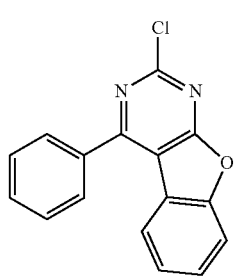

Sub 2(4b)
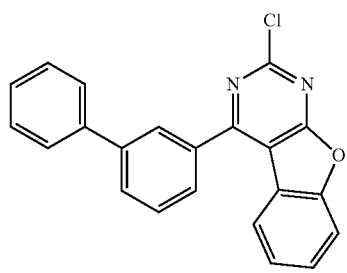
Sub 2(4c)
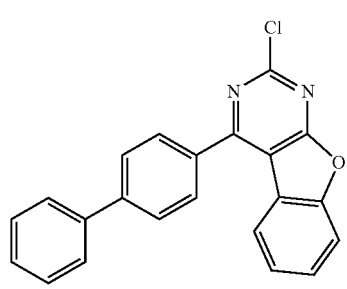
Sub 2(4d)
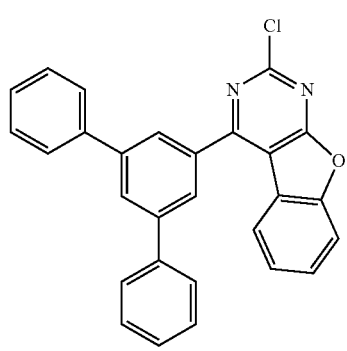
Sub 2(4e)
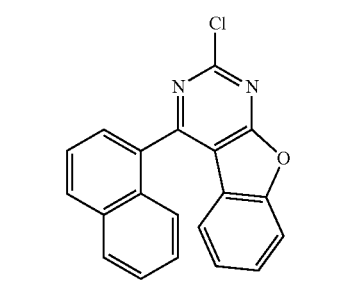
Sub 2(4f)
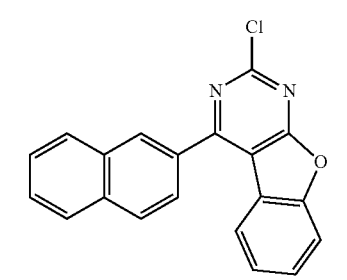
Sub 2(4g)
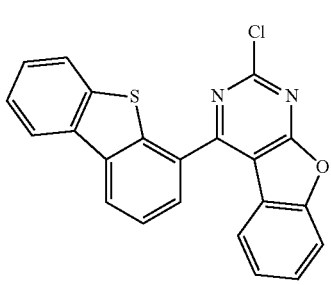
Sub 2(4h)
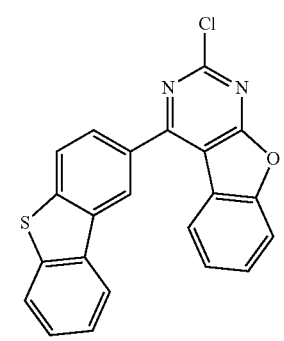
Sub 2(4i)
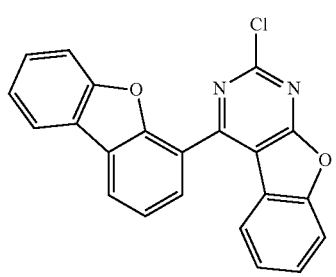
Sub 2(4j)
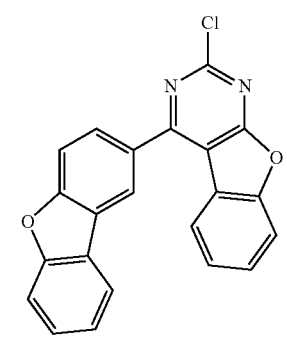
Sub 2(4k)
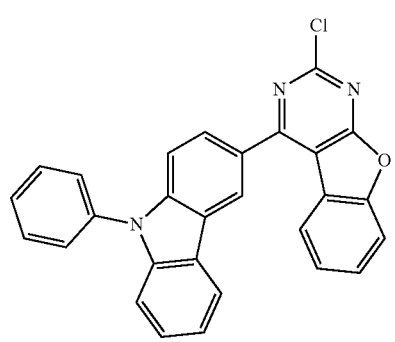

Sub 2(4l)

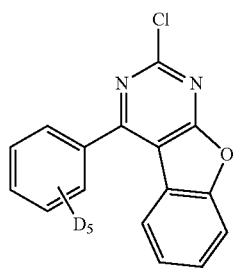

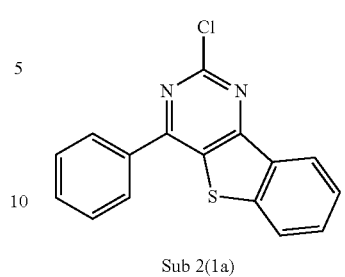

Sub 2(1a)

TABLE 1

| Compound | FD-MS | Compound | FD-MS |
|---|---|---|---|
| Sub 2(1a) | m/z = 296.77($C_{16}H_9ClN_2S$ = 296.02) | Sub 2(1b) | m/z = 372.87($C_{22}H_{13}ClN_2S$ = 372.05) |
| Sub 2(1c) | m/z = 372.87($C_{22}H_{13}ClN_2S$ = 372.05) | Sub 2(1d) | m/z = 448.97($C_{28}H_{17}ClN_2S$ = 448.08) |
| Sub 2(1e) | m/z = 346.83($C_{20}H_{11}ClN_2S$ = 346.03) | Sub 2(1f) | m/z = 346.83($C_{20}H_{11}ClN_2S$ = 346.03) |
| Sub 2(1g) | m/z = 402.92($C_{22}H_{11}ClN_2S_2$ = 402.01) | Sub 2(1h) | m/z = 402.92($C_{22}H_{11}ClN_2S_2$ = 296.02) |
| Sub 2(1i) | m/z = 386.85($C_{22}H_{11}ClN_2OS$ = 386.03) | Sub 2(1j) | m/z = 386.85($C_{22}H_{11}ClN_2OS$ = 386.03) |
| Sub 2(1k) | m/z = 461.96($C_{28}H_{16}ClN_3S$ = 461.08) | Sub 2(1l) | m/z = 321.88($C_{17}H_{12}D_5ClN_2S$ = 321.11) |
| Sub 2(2a) | m/z = 296.77($C_{16}H_9ClN_2S$ = 296.02) | Sub 2(2b) | m/z = 372.87($C_{22}H_{13}ClN_2S$ = 372.05) |
| Sub 2(2c) | m/z = 372.87($C_{22}H_{13}ClN_2S$ = 372.05) | Sub 2(2d) | m/z = 448.97($C_{28}H_{17}ClN_2S$ = 448.08) |
| Sub 2(2e) | m/z = 346.83($C_{20}H_{11}ClN_2S$ = 346.03) | Sub 2(2f) | m/z = 346.83($C_{20}H_{11}ClN_2S$ = 346.03) |
| Sub 2(2g) | m/z = 402.92($C_{22}H_{11}ClN_2S_2$ = 402.01) | Sub 2(2h) | m/z = 402.92($C_{22}H_{11}ClN_2S_2$ = 296.02) |
| Sub 2(2i) | m/z = 386.85($C_{22}H_{11}ClN_2OS$ = 386.03) | Sub 2(2j) | m/z = 386.85($C_{22}H_{11}ClN_2OS$ = 386.03) |
| Sub 2(2k) | m/z = 461.96($C_{28}H_{16}ClN_3S$ = 461.08) | Sub 2(2l) | m/z = 321.88($C_{17}H_{12}D_5ClN_2S$ = 321.11) |
| Sub 2(3a) | m/z = 280.71($C_{16}H_9ClN_2O$ = 280.04) | Sub 2(3b) | m/z = 356.88($C_{22}H_{13}ClN_2O$ = 356.07) |
| Sub 2(3c) | m/z = 356.88($C_{22}H_{13}ClN_2O$ = 356.07) | Sub 2(3d) | m/z = 432.90($C_{28}H_{17}ClN_2O$ = 432.10) |
| Sub 2(3e) | m/z = 330.77($C_{20}H_{11}ClN_2O$ = 330.06) | Sub 2(3f) | m/z = 330.77($C_{20}H_{11}ClN_2O$ = 330.06) |
| Sub 2(3g) | m/z = 386.85($C_{22}H_{11}ClN_2OS$ = 386.03) | Sub 2(3h) | m/z = 386.85($C_{22}H_{11}ClN_2OS$ = 386.03) |
| Sub 2(3i) | m/z = 370.79($C_{22}H_{11}ClN_2O_2$ = 370.05) | Sub 2(3j) | m/z = 370.79($C_{22}H_{11}ClN_2O_2$ = 370.05) |
| Sub 2(3k) | m/z = 445.90($C_{28}H_{16}ClN_2O$ = 445.10) | Sub 2(3l) | m/z = 305.81($C_{17}H_{12}D_5ClN_2O$ = 305.13) |
| Sub 2(4a) | m/z = 280.71($C_{16}H_9ClN_2O$ = 280.04) | Sub 2(4b) | m/z = 356.88($C_{22}H_{13}ClN_2O$ = 356.07) |
| Sub 2(4c) | m/z = 356.88($C_{22}H_{13}ClN_2O$ = 356.07) | Sub 2(4d) | m/z = 432.90($C_{28}H_{17}ClN_2O$ = 432.10) |
| Sub 2(4e) | m/z = 330.77($C_{20}H_{11}ClN_2O$ = 330.06) | Sub 2(4f) | m/z = 330.77($C_{20}H_{11}ClN_2O$ = 330.06) |
| Sub 2(4g) | m/z = 386.85($C_{22}H_{11}ClN_2OS$ = 386.03) | Sub 2(4h) | m/z = 386.85($C_{22}H_{11}ClN_2OS$ = 386.03) |
| Sub 2(4i) | m/z = 370.79($C_{22}H_{11}ClN_2O_2$ = 370.05) | Sub 2(4j) | m/z = 370.79($C_{22}H_{11}ClN_2O_2$ = 370.05) |
| Sub 2(4k) | m/z = 445.90($C_{28}H_{16}ClN_2O$ = 445.10) | Sub 2(4l) | m/z = 305.81($C_{17}H_{12}D_5ClN_2O$ = 305.13) |

Synthesis Example of Final Product

Synthesis Example of Compound 1

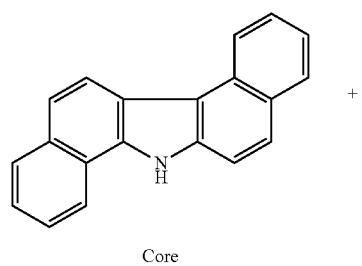

Core

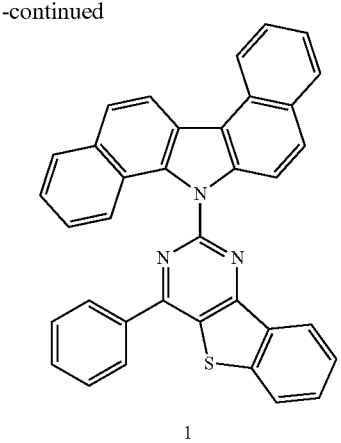

1

After dissolving Core (12.6 g, 47.3 mmol) in toluene (500 mL) in a round bottom flask, Sub 2(1a) (15.4 g, 52.0 mmol), Pd$_2$(dba)$_3$ (2.2 g, 2.4 mmol), P(t-Bu)$_3$ (1 g, 4.73 mmol) and NaOt-Bu (13.6 g, 141.8 mmol) were added and the mixture was stirred at 100° C. When the reaction was completed, the reaction product was extracted with CH$_2$Cl$_2$ and water, and the organic layer was dried with MgSO$_4$ and concentrated. Thereafter, the concentrate was passed through a silica gel column and recrystallized to obtain 21.2 g (yield: 85%) of the product.

Synthesis Example of Compound 11

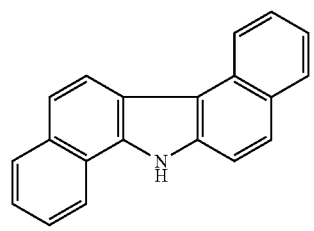

Core

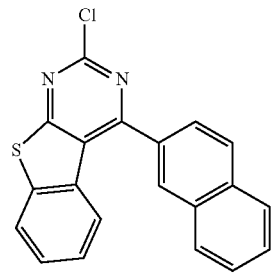

Sub 2(2f)

Core (12.6 g, 47.3 mmol) and Sub 2(2f) (18.0 g, 52.0 mmol) were reacted as in the synthesis method of the product 1 to obtain 21.6 g (yield: 79%) of the product.

Synthesis Example of Compound 18

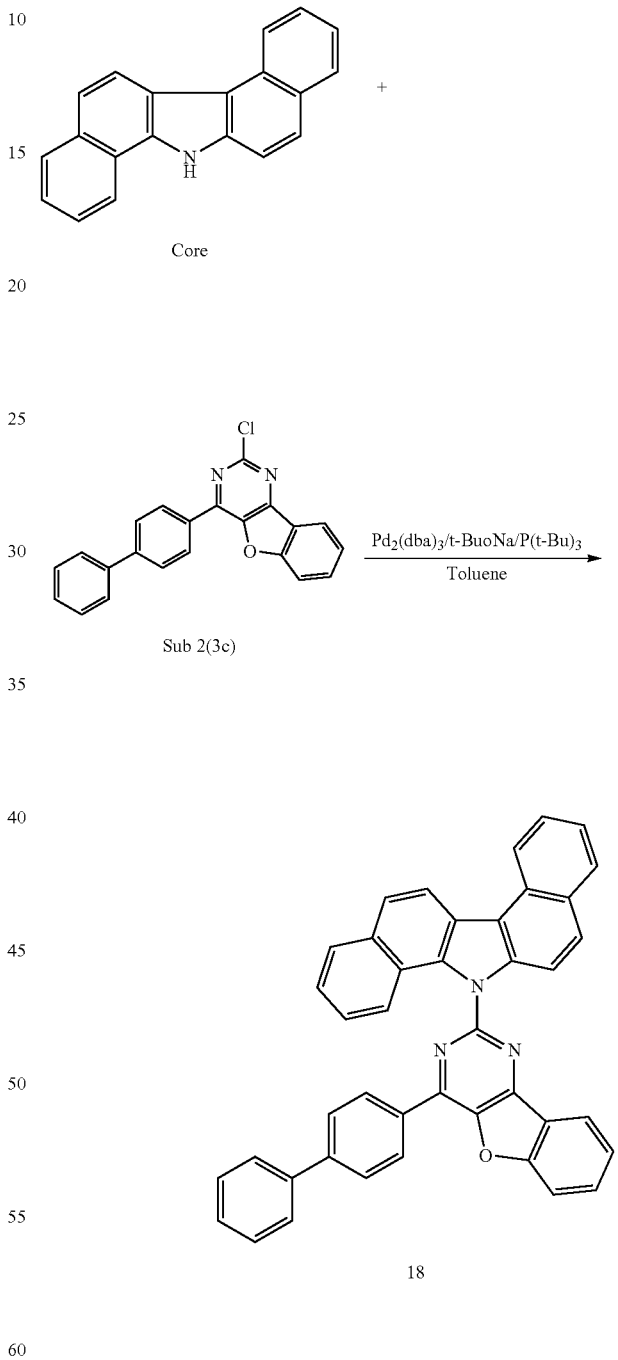

Core (12.6 g, 47.3 mmol) and Sub 2(3c) (18.6 g, 52.0 mmol) were reacted as in the synthesis method of the product 1 to obtain 22.2 g (yield: 80%) of the product.

Synthesis Example of Compound 32

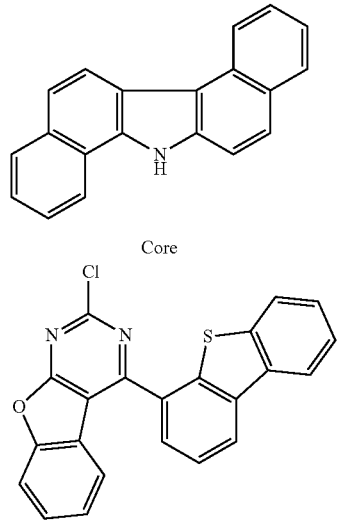

Core

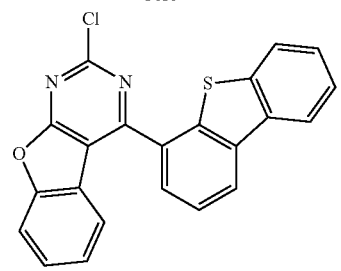

Sub 2(4g)

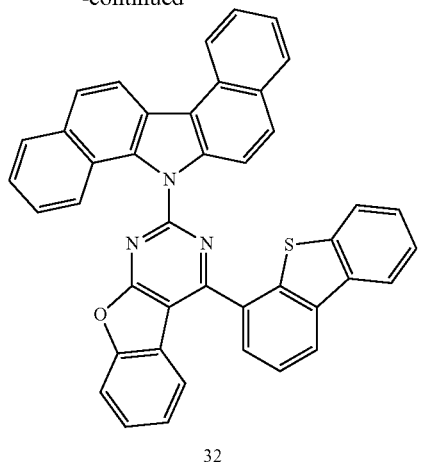

32

Core (12.6 g, 47.3 mmol) and Sub 2 (4 g) (19.0 g, 52.0 mmol) were reacted as in the synthesis method of the product 1 to obtain 23.4 g (yield: 80%) of the product.

The FD-MS values of the compounds 1 to 60 of the present invention prepared according to the above synthesis examples are shown in the following Table 2.

TABLE 2

| Compound | FD-MS | Compound | FD-MS |
|---|---|---|---|
| 1 | m/z = 527.2($C_{36}H_{21}N_3S$ = 527.7) | 2 | m/z = 511.2($C_{36}H_{21}N_3O$ = 511.6) |
| 3 | m/z = 527.2($C_{36}H_{21}N_3S$ = 527.7) | 4 | m/z = 511.2($C_{36}H_{21}N_3O$ = 511.6) |
| 5 | m/z = 577.2($C_{40}H_{23}N_3S$ = 577.7) | 6 | m/z = 561.2($C_{40}H_{23}N_3O$ = 561.6) |
| 7 | m/z = 577.2($C_{40}H_{23}N_3S$ = 577.7) | 8 | m/z = 561.2($C_{40}H_{23}N_3O$ = 561.6) |
| 9 | m/z = 577.2($C_{40}H_{23}N_3S$ = 577.7) | 10 | m/z = 561.2($C_{40}H_{23}N_3O$ = 561.6) |
| 11 | m/z = 577.2($C_{40}H_{23}N_3S$ = 577.7) | 12 | m/z = 561.2($C_{40}H_{23}N_3O$ = 561.6) |
| 13 | m/z = 627.2($C_{44}H_{25}N_3S$ = 627.8) | 14 | m/z = 611.2($C_{44}H_{25}N_3O$ = 611.7) |
| 15 | m/z = 627.2($C_{44}H_{25}N_3S$ = 627.8) | 16 | m/z = 611.2($C_{44}H_{25}N_3O$ = 611.7) |
| 17 | m/z = 603.2($C_{42}H_{25}N_3S$ = 603.7) | 18 | m/z = 587.2($C_{42}H_{25}N_3O$ = 587.7) |
| 19 | m/z = 603.2($C_{42}H_{25}N_3S$ = 603.7) | 20 | m/z = 587.2($C_{42}H_{25}N_3O$ = 587.7) |
| 21 | m/z = 603.2($C_{42}H_{25}N_3S$ = 603.7) | 22 | m/z = 587.2($C_{42}H_{25}N_3O$ = 587.7) |
| 23 | m/z = 603.2($C_{42}H_{25}N_3S$ = 603.7) | 24 | m/z = 587.2($C_{42}H_{25}N_3O$ = 587.7) |
| 25 | m/z = 603.2($C_{42}H_{25}N_3S$ = 603.7) | 26 | m/z = 587.2($C_{42}H_{25}N_3O$ = 587.7) |
| 27 | m/z = 603.2($C_{42}H_{25}N_3S$ = 603.7) | 28 | m/z = 587.2($C_{42}H_{25}N_3O$ = 587.7) |
| 29 | m/z = 633.1($C_{42}H_{23}N_3S_2$ = 633.8) | 30 | m/z = 617.2($C_{42}H_{23}N_3O_1S_1$ = 617.7) |
| 31 | m/z = 633.1($C_{42}H_{23}N_3S_2$ = 633.8) | 32 | m/z = 617.2($C_{42}H_{23}N_3O_1S_1$ = 617.7) |
| 33 | m/z = 617.2($C_{42}H_{23}N_3S_1O_1$ = 617.7) | 34 | m/z = 601.2($C_{42}H_{24}N_3O_2$ = 601.7) |
| 35 | m/z = 617.2($C_{42}H_{23}N_3S_1O_1$ = 617.7) | 36 | m/z = 601.2($C_{42}H_{24}N_3O_2$ = 601.7) |
| 37 | m/z = 616.2($C_{42}H_{24}N_4S$ = 616.7) | 38 | m/z = 600.2($C_{42}H_{24}N_4O$ = 600.7) |
| 39 | m/z = 616.2($C_{42}H_{24}N_4S$ = 616.7) | 40 | m/z = 600.2($C_{42}H_{24}N_4O$ = 600.7) |
| 41 | m/z = 681.2($C_{46}H_{27}N_5S$ = 681.8) | 42 | m/z = 665.2($C_{46}H_{27}N_5O$ = 665.8) |
| 43 | m/z = 681.2($C_{46}H_{27}N_5S$ = 681.8) | 44 | m/z = 665.2($C_{46}H_{27}N_5O$ = 665.8) |
| 45 | m/z = 682.2($C_{45}H_{26}N_6S$ = 682.8) | 46 | m/z = 666.2($C_{45}H_{25}N_6O$ = 666.7) |
| 47 | m/z = 682.2($C_{45}H_{26}N_6S$ = 682.8) | 48 | m/z = 666.2($C_{45}H_{25}N_6O$ = 666.7) |
| 49 | m/z = 577.2($C_{40}H_{22}N_3S$ = 577.7) | 50 | m/z = 561.2($C_{40}H_{23}N_3O$ = 561.6) |
| 51 | m/z = 577.2($C_{40}H_{22}N_3S$ = 577.7) | 52 | m/z = 561.2($C_{40}H_{23}N_3O$ = 561.6) |
| 53 | m/z = 577.2($C_{40}H_{22}N_3S$ = 577.7) | 54 | m/z = 561.2($C_{40}H_{23}N_3O$ = 561.6) |
| 55 | m/z = 577.2($C_{40}H_{22}N_3S$ = 577.7) | 56 | m/z = 561.2($C_{40}H_{23}N_3O$ = 561.6) |
| 57 | m/z = 532.2($C_{36}H_{26}N_3S$ = 532.7) | 58 | m/z = 516.2($C_{36}H_{26}N_3O$ = 516.6) |
| 59 | m/z = 469.1($C_{30}H_{16}N_3S_1F_1$ = 469.5) | 60 | m/z = 460.1($C_{31}H_{16}N_4O$ = 460.5) |

Fabrication and Evaluation of Organic Electronic Element

[Example 1] Red OLED (Host)

After vacuum-depositing $N^1$-(naphthalen-2-yl)-$N^4$,$N^4$-bis(4-(naphthalen-2-yl (phenyl)amino)phenyl)-$N^1$-phenylbenzene-1,4-diamine (abbreviated as "2-TNATA") film on an ITO layer (anode) to form a hole injection layer having a thickness of 60 nm, wherein the ITO layer was formed on a glass substrate, 4,4-bis[N-(1-naphthalenyl)-N-phenylamino (abbreviated as "NPD") film was vacuum-deposited with a thickness of 60 nm on the hole injection layer to form a hole transport layer.

Next, the compound 1 of the present invention as a host material and bis-(1-phenylisoquinolyl)iridium(III)acetylacetonate (hereinafter "(piq)$_2$Ir(acac)") as a dopant material in a weight ratio of 95:5 were deposited on the hole transport layer to form a light emitting layer with a thickness of 30 nm.

Subsequently, (1,1'-biphenyl-4-olato)bis(2-methyl-8-quinolinolato)aluminum (abbreviated as "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm on the hole blocking layer to form an electron transport layer.

Thereafter, LiF was deposited to a thickness of 0.2 nm on the electron transport layer to form an electron injection layer and then Al was deposited to a thickness of 150 nm on the electron injection layer to form a cathode.

[Example 2] to [Example 18]

The OLEDs were fabricated in the same manner as described in Example 1 except that the compounds of the present invention described in the following Table 3, instead of the compound 1 of the present invention, were used as host material of a light emitting layer.

[Comparative Example 1] to [Comparative Example 4]

The OLEDs were fabricated in the same manner as described in Example 1 except that the following Comparative Compounds A to D, instead of the compound 1 of the present invention, were used as as a host material of a light emitting layer.

<Comp. compd A>

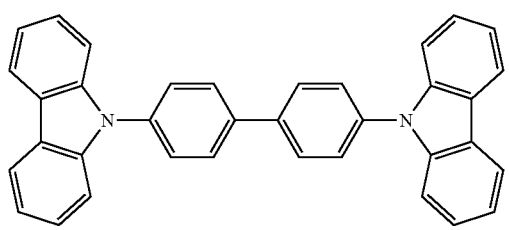

<Comp. compd B>

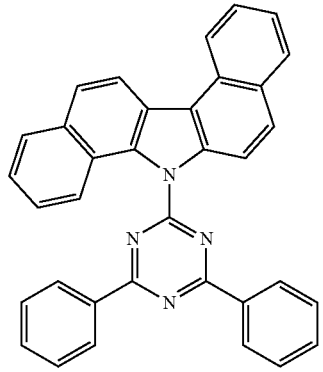

<Comp. compd C>

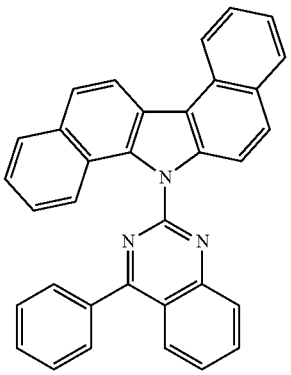

<Comp. compd D>

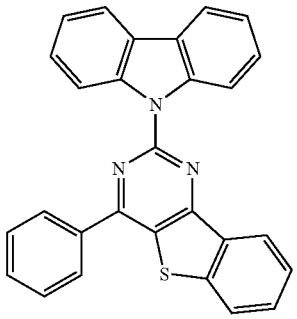

Electroluminescence (EL) characteristics were measured with a PR-650 (Photoresearch) by applying a forward bias DC voltage to the OLEDs prepared in Examples 1 to 18 of the present invention and Comparative Examples 1 to 4. And, the T95 life time was measured using a life time measuring apparatus manufactured by Mac science Inc. at reference brightness of 2500 cd/m$^2$. The measurement results are shown in Table 3 below.

TABLE 3

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(1) | comp. Com A | 6.2 | 34.7 | 2500.0 | 7.2 | 69.1 | 0.66 | 0.32 |
| comp. Ex(2) | comp. Com B | 5.9 | 26.6 | 2500.0 | 9.4 | 100.4 | 0.63 | 0.32 |
| comp. Ex(3) | comp. Com C | 5.7 | 23.4 | 2500.0 | 10.7 | 103.7 | 0.64 | 0.32 |
| comp. Ex(4) | comp. Com D | 6.0 | 28.1 | 2500.0 | 8.9 | 98.2 | 0.62 | 0.34 |
| Ex. (1) | Com. 1 | 5.1 | 14.2 | 2500.0 | 17.6 | 116.8 | 0.60 | 0.31 |
| Ex. (2) | Com. 2 | 5.3 | 12.9 | 2500.0 | 19.3 | 114.8 | 0.61 | 0.31 |
| Ex. (3) | Com. 3 | 5.3 | 14.1 | 2500.0 | 17.7 | 114.4 | 0.61 | 0.32 |
| Ex. (4) | Com. 4 | 5.1 | 12.9 | 2500.0 | 19.3 | 113.9 | 0.63 | 0.33 |
| Ex. (5) | Com. 5 | 5.2 | 13.9 | 2500.0 | 18.0 | 111.5 | 0.63 | 0.30 |
| Ex. (6) | Com. 10 | 5.1 | 14.4 | 2500.0 | 17.4 | 113.7 | 0.60 | 0.35 |
| Ex. (7) | Com. 15 | 5.2 | 14.6 | 2500.0 | 17.1 | 110.5 | 0.64 | 0.34 |
| Ex. (8) | Com. 20 | 5.1 | 12.9 | 2500.0 | 19.5 | 114.1 | 0.62 | 0.32 |
| Ex. (9) | Com. 23 | 5.1 | 14.0 | 2500.0 | 17.9 | 110.9 | 0.63 | 0.33 |
| Ex. (10) | Com. 26 | 5.2 | 13.8 | 2500.0 | 18.1 | 113.9 | 0.64 | 0.30 |
| Ex. (11) | Com. 32 | 5.4 | 15.8 | 2500.0 | 15.9 | 114.8 | 0.65 | 0.33 |
| Ex. (12) | Com. 35 | 5.4 | 17.7 | 2500.0 | 14.1 | 113.6 | 0.64 | 0.31 |
| Ex. (13) | Com. 40 | 5.4 | 16.7 | 2500.0 | 14.9 | 114.4 | 0.64 | 0.31 |
| Ex. (14) | Com. 41 | 5.3 | 15.9 | 2500.0 | 15.7 | 113.8 | 0.62 | 0.31 |
| Ex. (15) | Com. 48 | 5.5 | 16.4 | 2500.0 | 15.3 | 119.0 | 0.64 | 0.34 |
| Ex. (16) | Com. 51 | 5.4 | 16.1 | 2500.0 | 15.5 | 113.4 | 0.61 | 0.34 |
| Ex. (17) | Com. 54 | 5.4 | 15.8 | 2500.0 | 15.8 | 111.8 | 0.64 | 0.32 |
| Ex. (18) | Com. 57 | 5.1 | 13.7 | 2500.0 | 18.2 | 116.6 | 0.63 | 0.30 |

As can be seen from the results of Table 3, the driving voltage, luminous efficiency and lifetime are significantly improved, which are electrical characteristics of the organic electroluminescent element, are significantly improved when the material for an organic electroluminescent device of the present invention is used as a phosphorescent host, compared to the case of using Comparative Compounds A to D.

Comparative Compound A is CBP that is commonly used as a host material. The characteristics of the element were excellent when using Comparative Compound B to Comparative Compound D as a host rather than Comparative Compound A. In addition, the characteristics of the element were further improved when Comparative Compound B or Comparative Compound C, in which in which benzene is fused to both benzene rings of carbazole, was used as host materials rather than Comparative Compound D.

Comparative Compound B and Comparative Compound C differ only in the substituent attached to N of the same core having a carbazole derivative. The characteristics of the organic electroluminescent element are improved when using a Comparative Compound C rather than Comparative Compound B as a host material, wherein Comparative Compound B has a simple triazine having an electron transfer property (ET), and Comparative Compound C has a quinazoline bound to the same core.

In addition, the characteristics of the element were significantly improved when the compound of the present invention was used as the host material rather than the comparative compound C, wherein the compound of the present invention has benzothienopyrimidine or benzofuropyrimidine bound to N of the same carbazole derivative core.

From these results, even if the structure is similar, the type and position of the substituent plays a decisive role in the difference of properties, and the difference of these properties acts as a major factor (e.g., energy balance) in improving performance of device during device deposition. Accordingly, it can be seen that the result of device measurement, which is difficult for a person skilled in the art to derive, can be obtained.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

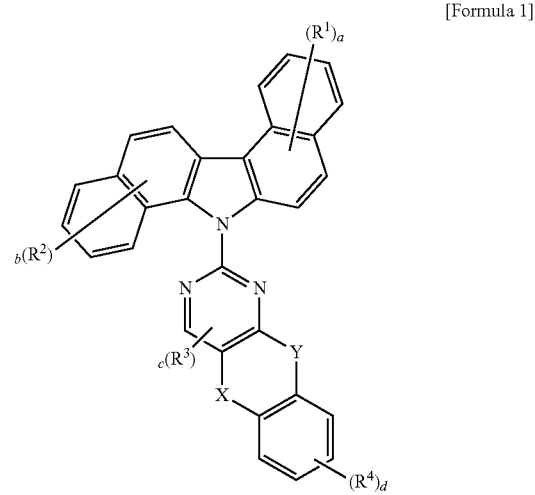

[Formula 1]

wherein:

R$^1$ and R$^2$ are each hydrogen or deuterium,

R$^3$ and R$^4$ are each independently selected from the group consisting of hydrogen, deuterium, halogen, a C$_6$-C$_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent $R^4$ groups together may be bonded to each other to form a $C_6$-$C_{60}$ aromatic ring or a $C_2$-$C_{60}$ heterocycle, a and b represent an integer of 0 to 6, c represents an integer of 0 or 1, d represents an integer of 0 to 4, X and Y are each independently a single bond, O or S, and at least one of X and Y is O or S, L' is selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring, and a $C_2$-$C_{60}$ heterocyclic group, $R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, and the above $R^1$ to $R^4$, L', $R_a$, $R_b$, and a ring formed by adjacent $R^4$ groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, wherein Formula 1 is represented by Formula 2 or Formula 3:

<Formula 2>

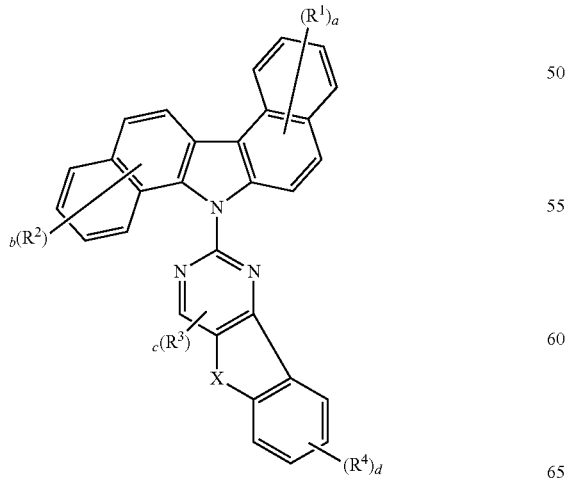

<Formula 3>

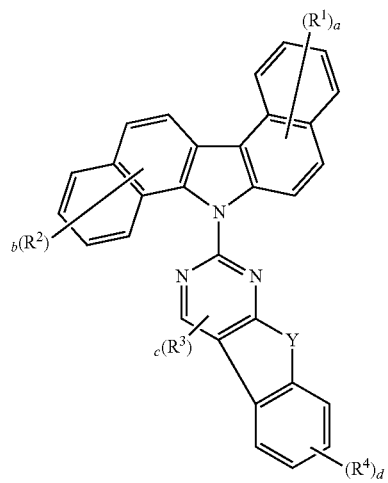

wherein $R^1$ to $R^4$, a, b, c, d, X and Y are the same as defined in claim 1.

3. The compound of claim 1, wherein the compound represented by Formula 1 is one of the following compounds:

1

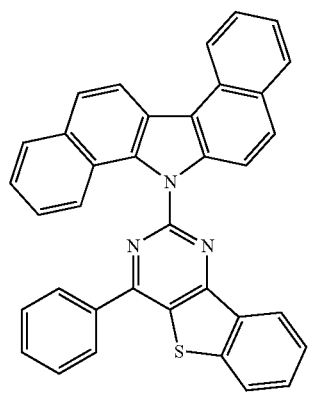

2

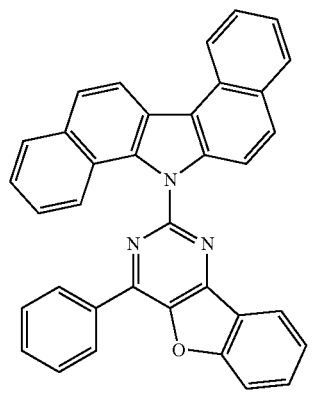

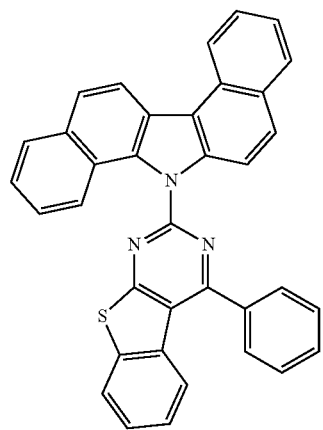
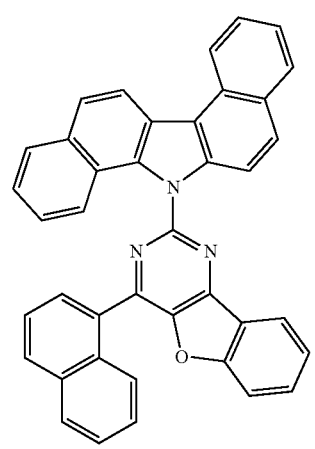
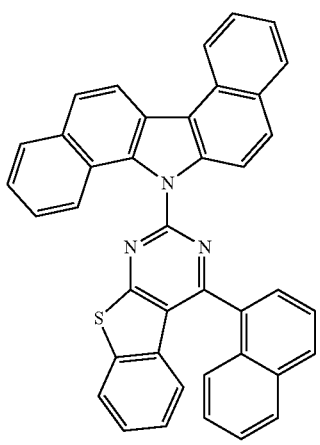
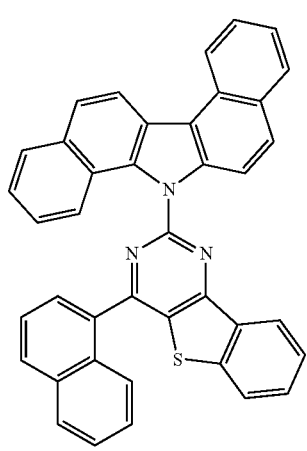

9
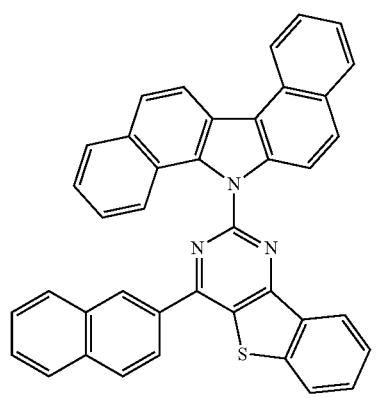
10
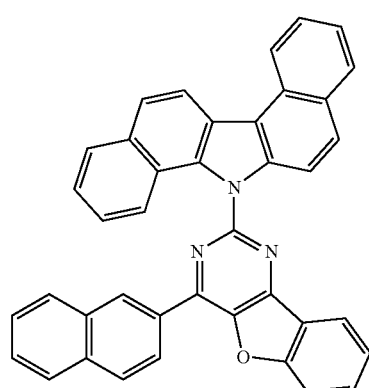
11
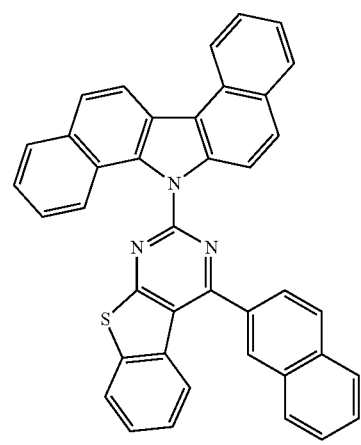
12
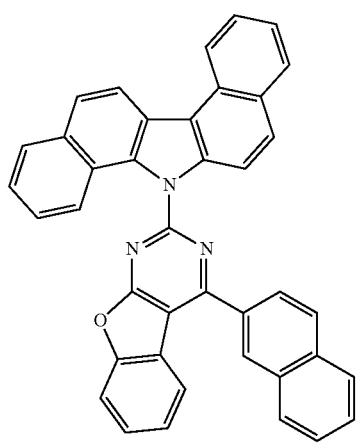
13
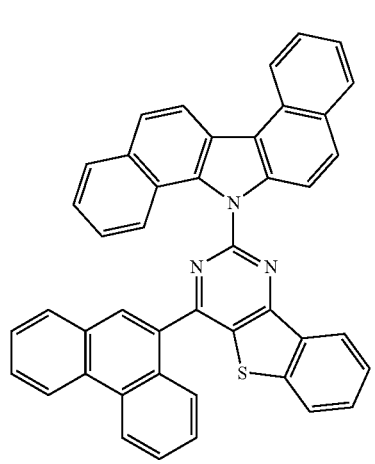
14
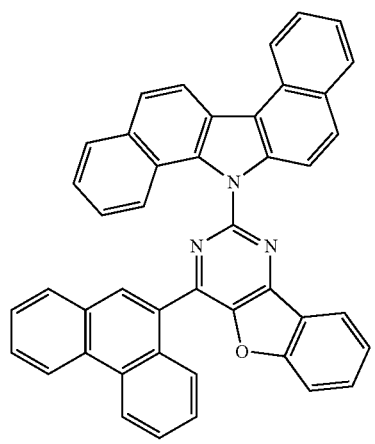

15
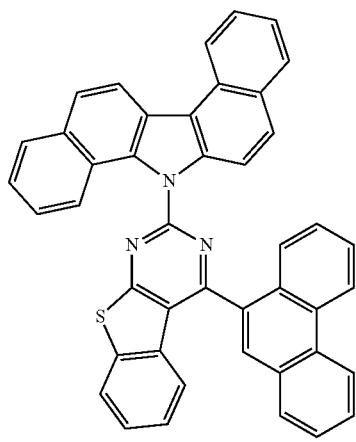
16
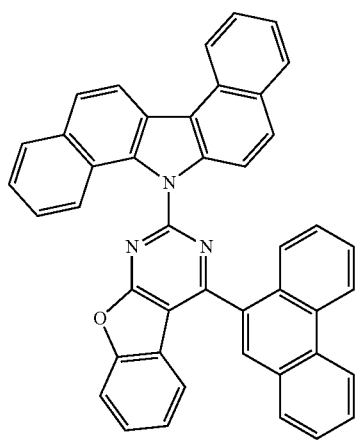
17
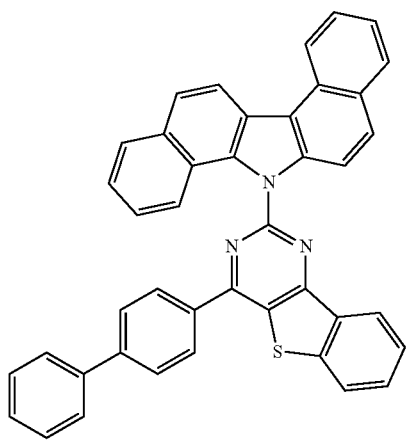
18
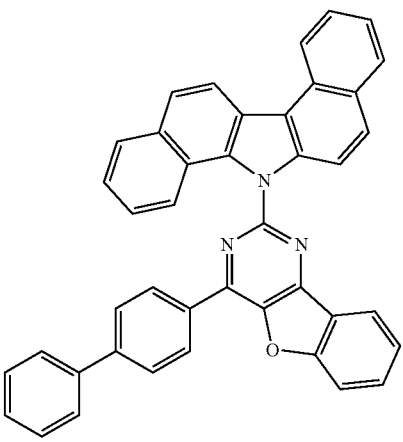
19
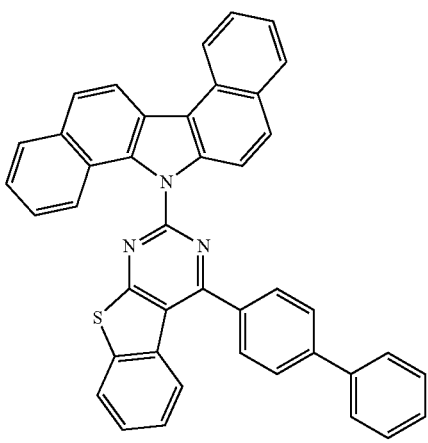
20
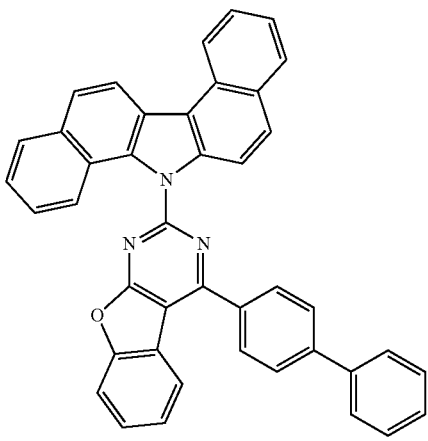

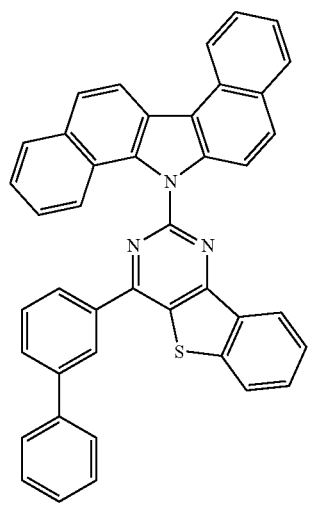
21
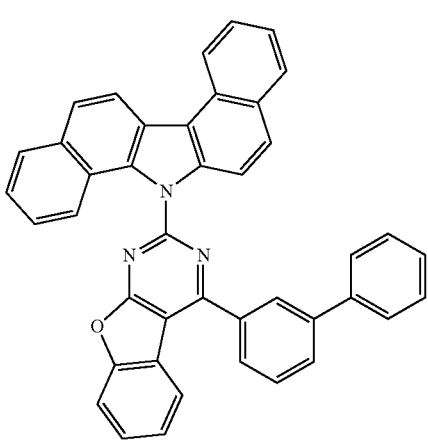
24
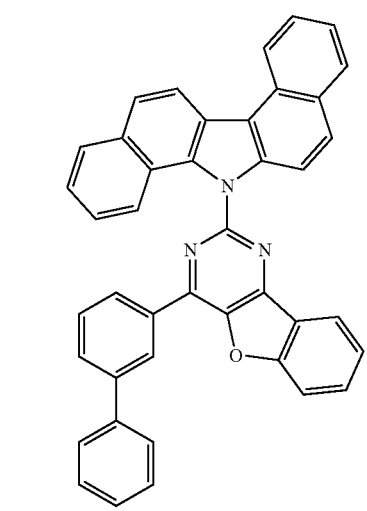
22
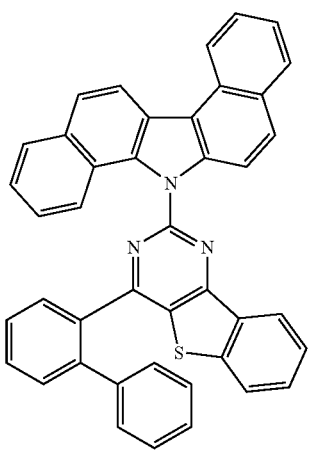
25
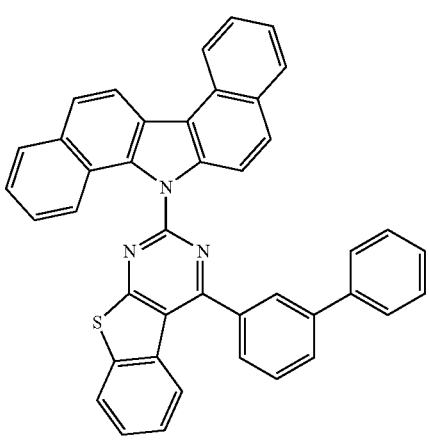
23
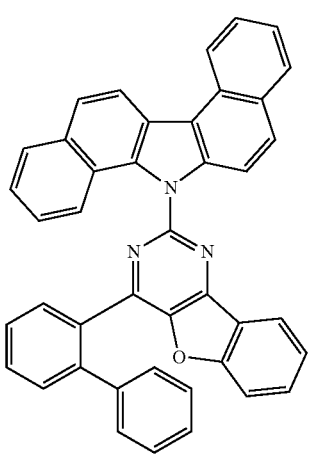
26

27
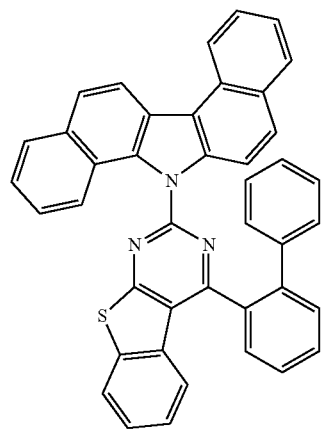
28
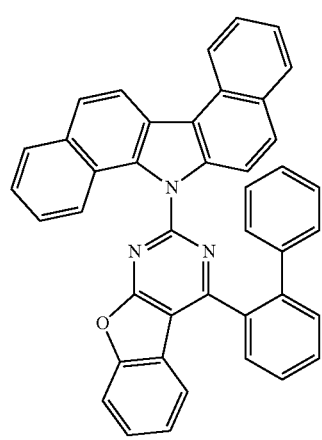
29
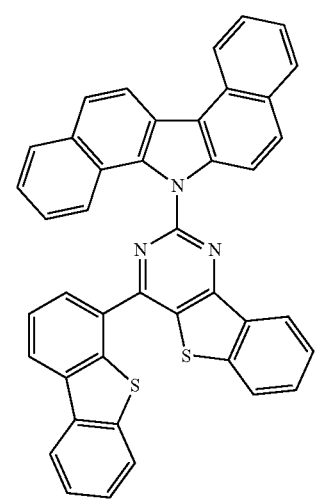
30
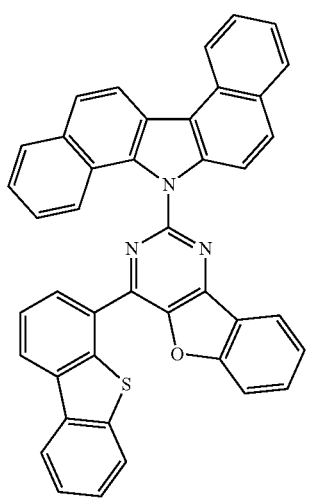
31
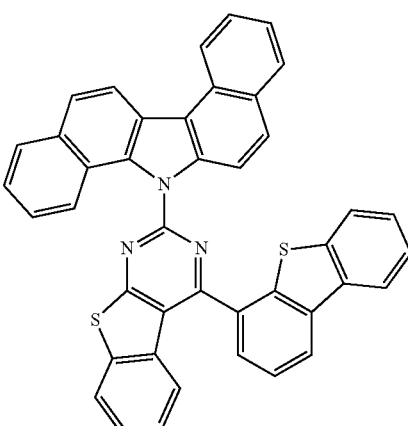
32
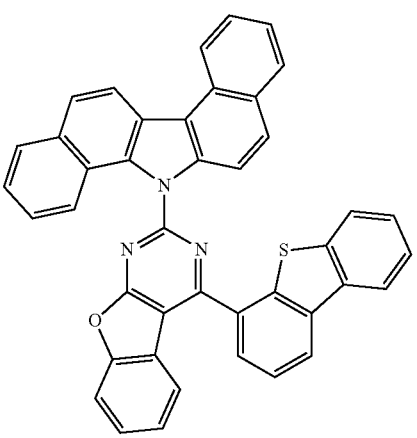

33
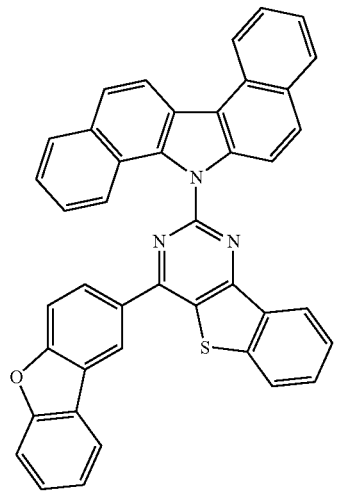
34
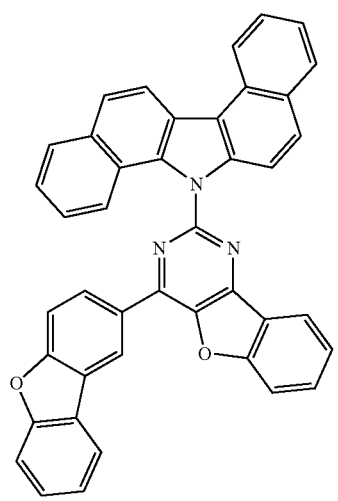
35
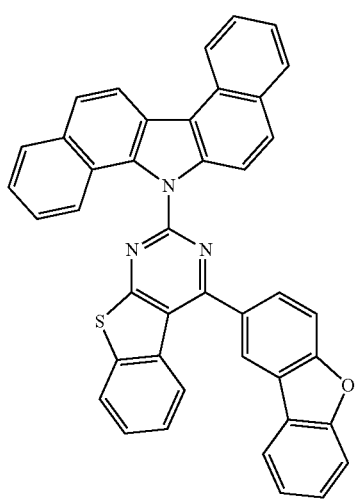
36
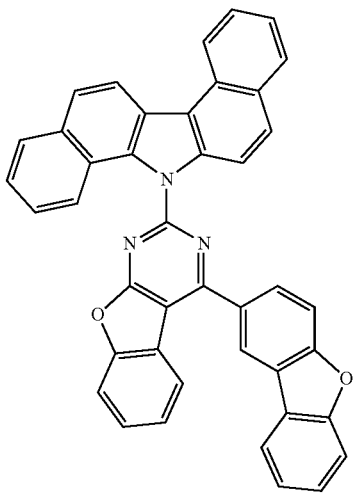
37
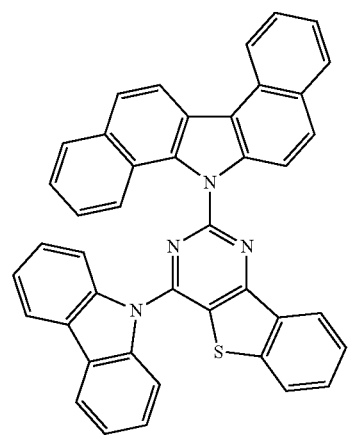
38
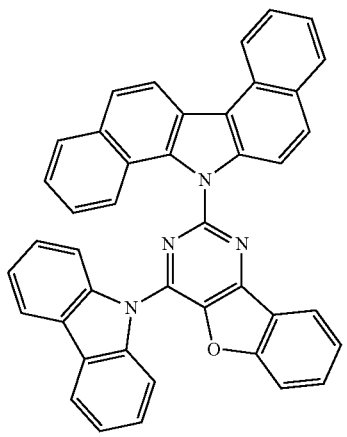

39
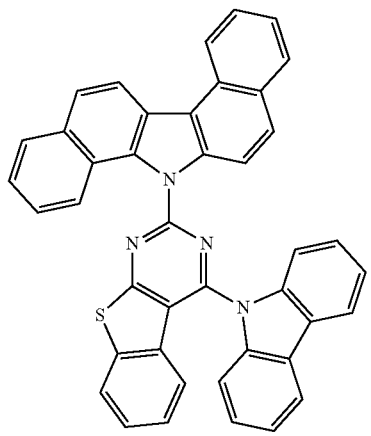
40
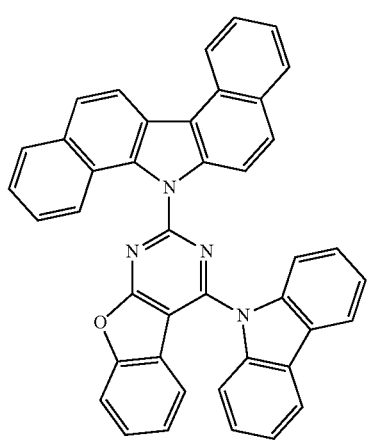
41
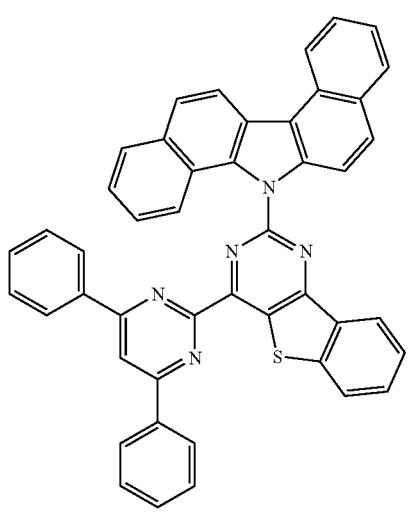
42
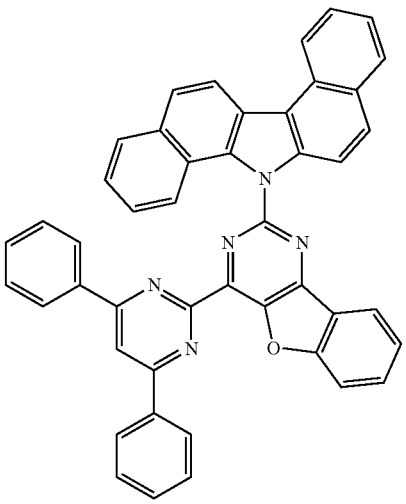
43
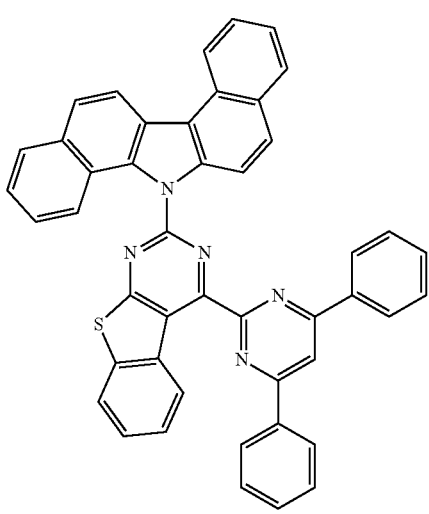
44
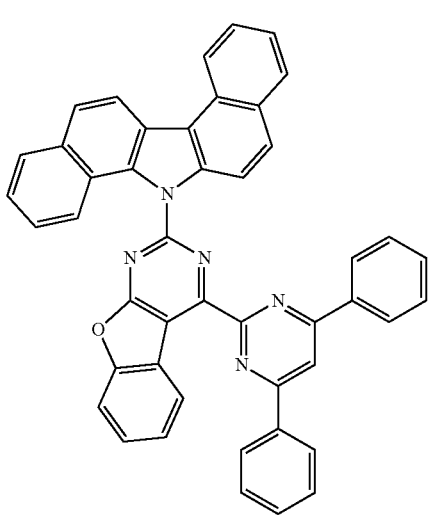

-continued
45
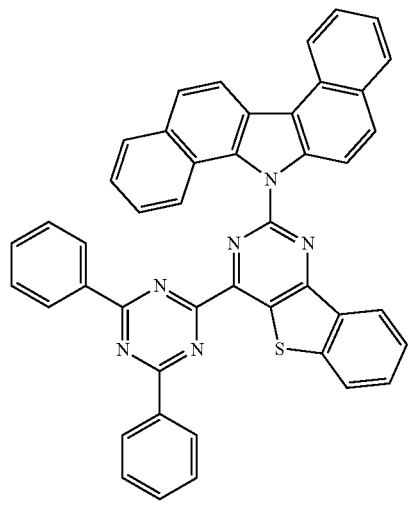
46
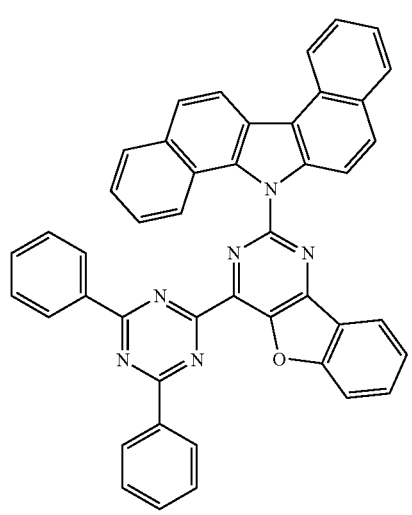
47
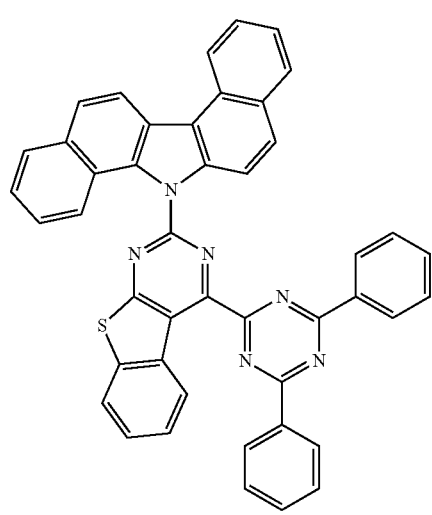
-continued
48
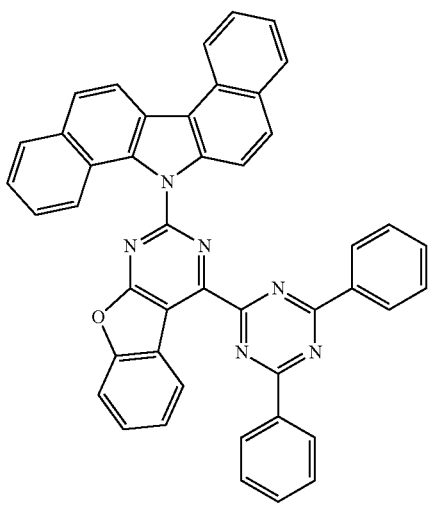
49
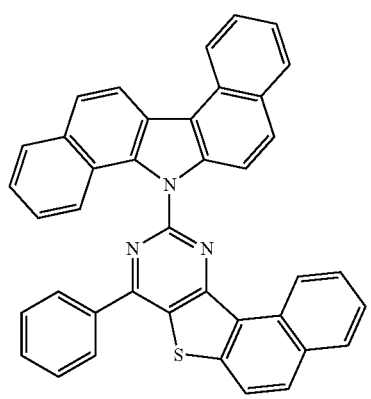
50
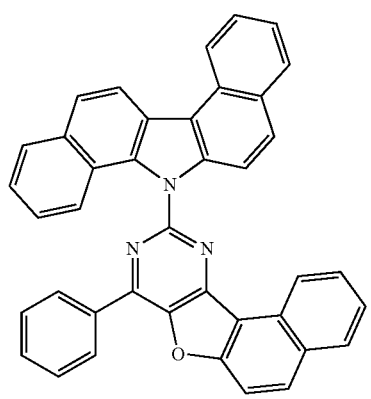

51
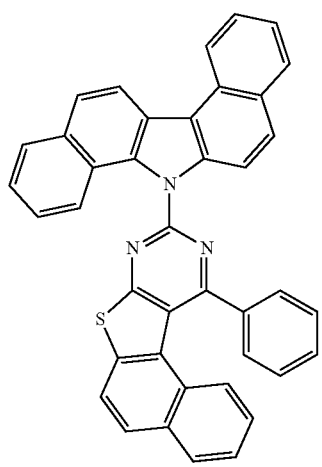
52
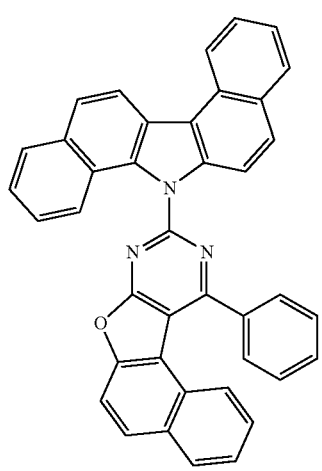
53
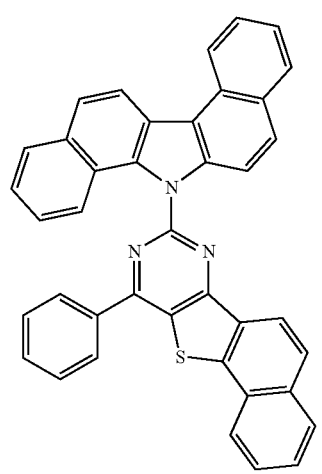
54
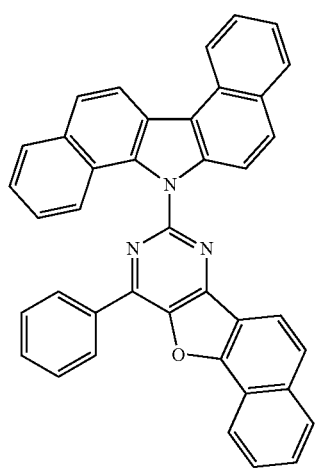
55
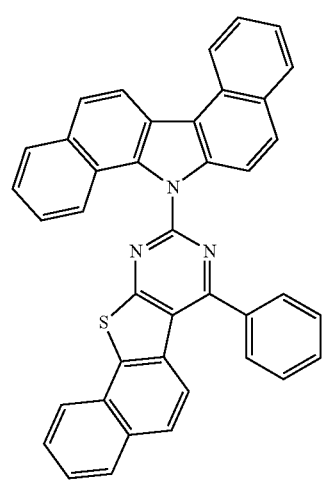
56
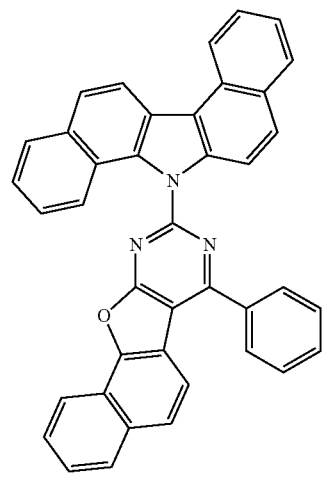

57

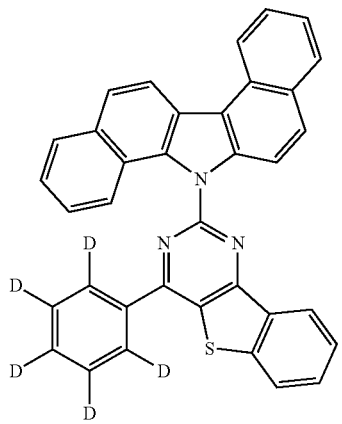

58

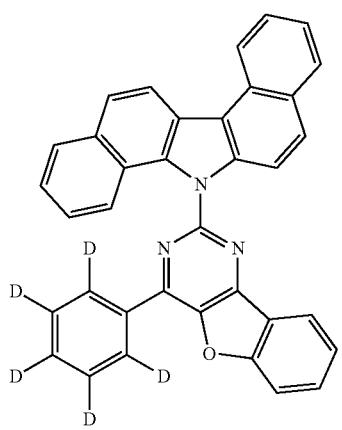

59

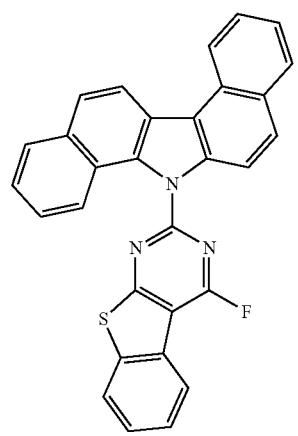

60

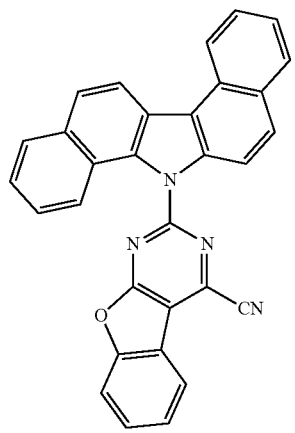

4. An organic electroluminescent element comprising a first electrode, a second electrode, and an organic material layer formed between the first electrode and the second electrode, wherein the organic material layer comprises the compound of claim 1.

5. The organic electroluminescent element of claim 4, wherein the compound is comprised as a single compound or a mixture.

6. The organic electroluminescent element of claim 4, wherein the organic material layer comprises at least one of a hole injection layer, a hole transport layer, an emission-auxiliary layer, a light emitting layer, an electron transport auxiliary layer, an electron transport layer and an electron injection layer, and the compound represented by the Formula 1 is comprised in the light emitting layer.

7. The organic electroluminescent element of claim 4, wherein the organic material layer is formed by a process of spin coating, nozzle printing, inkjet printing, slot coating, dip coating or roll-to-roll.

8. The organic electroluminescent element of claim 4, wherein the organic electroluminescent element further comprises a layer for improving luminous efficiency formed on one side of sides of the first electrode or the second electrode, and the one side is not facing the organic material layer.

9. An electronic device comprising a display device and a control unit for driving the display device, wherein the display device comprises the organic electroluminescent element of claim 4.

10. The electronic device of claim 9, wherein the organic electroluminescent element is selected from the group consisting of an organic light emitting diode, an organic solar cell, an organic photo conductor, an organic transistor, an element for monochromatic illumination and element for quantum dot display.

* * * * *